United States Patent
Park et al.

(10) Patent No.: US 9,977,006 B2
(45) Date of Patent: May 22, 2018

(54) HYDROGEN SENSOR ELEMENT FOR MEASURING CONCENTRATION OF HYDROGEN GAS DISSOLVED IN LIQUID AND METHOD FOR MEASURING CONCENTRATION OF HYDROGEN GAS USING SAME

(71) Applicant: KOREA ADVANCED INSTITUTE OF SCIENCE AND TECHNOLOGY, Daejeon (KR)

(72) Inventors: Chong Ook Park, Daejeon (KR); Seong Wan Kim, Daejeon (KR); Dae Ro Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 99 days.

(21) Appl. No.: 15/021,609

(22) PCT Filed: Sep. 11, 2014

(86) PCT No.: PCT/KR2014/008461
§ 371 (c)(1),
(2) Date: Apr. 29, 2016

(87) PCT Pub. No.: WO2015/037910
PCT Pub. Date: Mar. 19, 2015

(65) Prior Publication Data
US 2016/0231303 A1  Aug. 11, 2016

(30) Foreign Application Priority Data

Sep. 12, 2013 (KR) .................... 10-2013-0109828
Jan. 17, 2014 (KR) .................... 10-2014-0006159
Jul. 22, 2014 (KR) .................... 10-2014-0092371

(51) Int. Cl.
*G01N 33/28* (2006.01)
*G01N 27/404* (2006.01)
(Continued)

(52) U.S. Cl.
CPC ..... *G01N 33/2841* (2013.01); *G01N 27/4045* (2013.01); *G01N 27/4074* (2013.01); *G01N 27/4114* (2013.01); *G01N 33/005* (2013.01)

(58) Field of Classification Search
CPC ............ G01N 27/4045; G01N 33/005; G01N 33/2841; G01N 27/4074; G01N 27/4114
See application file for complete search history.

(56) References Cited

U.S. PATENT DOCUMENTS 3,325,378 A * 6/1967 Greene .............. G01N 27/4045
204/290.08
4,271,474 A * 6/1981 Belanger ............ G01N 27/4045
204/406
(Continued)

FOREIGN PATENT DOCUMENTS

CN       101523200 A   9/2009
EP       1376117 A1    2/2004
(Continued)

OTHER PUBLICATIONS

Cargol, Tim. "An overview of online oil monitoring technologies." Fourth Annual Weidmann-ACTI Technical Conference. 2005.*
(Continued)

*Primary Examiner* — Harshad R Patel
*Assistant Examiner* — Punam Roy

(57) ABSTRACT

The present invention couples a housing including a gas separation membrane to a sensor unit capable of detecting the concentration of hydrogen gas such that liquid cannot permeate a closed space within the housing and only hydrogen gas dissolved in the liquid can permeate the closed space
(Continued)

through the gas separation membrane, and detachably couples such a hydrogen sensor element to an opening of a container in which the liquid is held. Accordingly, the present invention can measure the concentration of dissolved hydrogen gas in a simple manner.

23 Claims, 15 Drawing Sheets

(51) Int. Cl.
*G01N 27/407* (2006.01)
*G01N 33/00* (2006.01)
*G01N 27/411* (2006.01)

(56) References Cited

U.S. PATENT DOCUMENTS

| | | | |
|---|---|---|---|
| 4,293,399 A | 10/1981 | Belanger et al. | |
| 4,578,154 A * | 3/1986 | Kitamura | G01N 27/404 204/406 |
| 4,661,211 A * | 4/1987 | Petty-Weeks | G01N 27/4074 204/424 |
| 6,277,329 B1 * | 8/2001 | Evans | G01N 33/0013 422/80 |
| 6,324,891 B1 * | 12/2001 | Gibeault | G01N 33/0014 73/19.01 |
| 6,787,014 B2 * | 9/2004 | Hasei | G01N 27/4074 204/424 |
| 7,276,141 B2 * | 10/2007 | Nadanami | G01N 27/4074 204/424 |
| 7,306,712 B2 * | 12/2007 | Watanabe | G01N 27/4114 204/424 |
| 8,273,229 B2 * | 9/2012 | Harada | C01B 3/001 204/431 |
| 8,836,523 B2 * | 9/2014 | Roy Trudel | H01H 9/0005 340/632 |
| 2003/0221975 A1 | 12/2003 | Mizutani et al. | |
| 2004/0112743 A1 | 6/2004 | Fukatsu et al. | |
| 2005/0029100 A1 | 2/2005 | Park et al. | |
| 2007/0068493 A1 * | 3/2007 | Pavlovsky | G01N 33/005 123/479 |
| 2007/0125153 A1 * | 6/2007 | Visel | G01N 27/127 73/31.05 |
| 2007/0240491 A1 * | 10/2007 | Pavlovsky | G01N 33/005 73/31.05 |
| 2009/0302857 A1 | 12/2009 | Harada et al. | |
| 2010/0077828 A1 | 4/2010 | Herz et al. | |
| 2010/0229628 A1 | 9/2010 | Aoki | |
| 2012/0125770 A1 * | 5/2012 | Harada | G01N 27/4074 204/408 |
| 2015/0247818 A1 * | 9/2015 | Silvester | G01N 27/4045 205/793 |

FOREIGN PATENT DOCUMENTS

| | | |
|---|---|---|
| JP | 1981-164459 | 4/1981 |
| JP | 02-001538 A | 1/1990 |
| JP | 03-077055 A | 4/1991 |
| JP | 03-276059 A | 12/1991 |
| JP | 03-276061 A | 12/1991 |
| JP | 04-175639 A | 6/1992 |
| JP | 04-96045 U | 8/1992 |
| JP | 05-307014 A | 11/1993 |
| JP | 07-225212 A | 8/1995 |
| JP | 08-201331 A | 8/1996 |
| JP | 2000-019152 A | 1/2000 |
| JP | 2000-088794 A | 3/2000 |
| JP | 2000-121601 A | 4/2000 |
| JP | 2002-139468 A | 5/2002 |
| JP | 2002-202281 A | 7/2002 |
| JP | 2004-053579 A | 2/2004 |
| JP | 2006-090812 A | 4/2006 |
| JP | 2006-513403 A | 4/2006 |
| JP | 2006-242603 A | 9/2006 |
| JP | 2007-047124 A | 2/2007 |
| JP | 2012-031967 A | 2/2012 |
| JP | 2012-504240 A | 2/2012 |
| KR | 10-2004-0067752 A | 7/2004 |
| KR | 10-2007-0070346 A | 7/2007 |
| KR | 10-2011-0016169 A | 2/2011 |
| KR | 10-1014010 B1 | 2/2011 |
| KR | 10-1221881 B1 | 1/2013 |
| KR | 10-2014-0026583 A | 3/2014 |
| WO | WO 2004/025289 A1 | 3/2004 |
| WO | WO 2006/037992 A1 | 4/2006 |
| WO | 2008018243 A1 | 2/2008 |
| WO | WO 2010/039345 A1 | 4/2010 |

OTHER PUBLICATIONS

European Search Report for Application No. 14844519.0, dated Mar. 13, 2017.
Ghenadii Korotcenkov et al., "Review of Electrochemical Hydrogen Sensors", Chem. Rev., 2009, pp. 1402-1433, vol. 109, American Chemical Society.
International Search Report for International Patent Application No. PCT/KR2014/008461 filed Sep. 11, 2014.
Extended European Search Report for EP Application No. 14844519.0 dated Jul. 28, 2017.

* cited by examiner

HYDROGEN SENSOR ELEMENT FOR MEASURING CONCENTRATION OF HYDROGEN GAS DISSOLVED IN LIQUID AND METHOD FOR MEASURING CONCENTRATION OF HYDROGEN GAS USING SAME

TECHNICAL FIELD

The present invention relates to a hydrogen sensor device for measuring a concentration of dissolved hydrogen gas in liquid and a method for measuring a concentration of dissolved hydrogen gas in the liquid using the same.

BACKGROUND ART

There is a case in which characteristics or a change in characteristics of liquid are performed by measuring a concentration of dissolved gas dissolved in the liquid. For example, as engine oil of a vehicle and oil used in a transformer or various mechanical devices deteriorates, a concentration of hydrogen gas increases, and as a result, when the concentration of the hydrogen gas in the oil is measured, whether the oil deteriorates can be sensed. In actual, it is reported that in the case of the transformer, when dissolved hydrogen of 1000 ppm or more is generated, there is a risk of explosion.

In order to measure the concentration of the dissolved hydrogen gas dissolved in the liquid, methods including an optical method, a viscosity measuring method, an electrochemical method, a gas chromatograph method, a gas separation method, and the like may be used, but the methods are not a method that can measure a state of the liquid to be measured in real time, and as a result, when it is necessary to determine whether the oil deteriorates on the spot in real time, for example, the methods cannot be methods suitable for application to determine whether the oil deteriorates, and the like. Moreover, in the methods, a measurement device and a measurement process are complicated and besides, there are a lot of problems including a measurement method in that a long-time measurement time is required and high-priced equipment is required, and the like.

Therefore, a device and a method are required, which can sense whether the oil deteriorates by simply measuring the concentration of the dissolved hydrogen gas in the liquid such as the oil in real time.

DISCLOSURE

Technical Problem

The present invention is contrived to solve the problem and an object of the present invention is to provide a hydrogen sensor device which can simply measure a concentration of dissolved hydrogen gas in liquid in real time without high-priced complicated equipment.

Further, another object of the present invention is to provide a hydrogen sensor device which prevents a hydrogen sensor, in particular, a sensing electrode of the hydrogen sensor from being degraded due to exposure to the liquid.

In addition, yet another object of the present invention is to provide a hydrogen sensor device which can minimize an influence of accuracy of measurement from presence of other gases other than hydrogen in measuring the concentration of the dissolved hydrogen gas.

Moreover, still yet another object of the present invention is to provide a hydrogen sensor device and a method for measuring a concentration of hydrogen gas which can secure accuracy and reproducibility of measurement and allows a user to know a measurement result even from a long distance.

Technical Solution

In order to achieve the object, according to one aspect of the present invention, a hydrogen sensor device for measuring a concentration of dissolved hydrogen gas in liquid includes: a sensor unit measuring a concentration of hydrogen gas; and a housing coupled to the sensor unit and including a housing body having an opening portion formed in at least a part thereof and a gas separation film coupled to the opening portion to be gaseously and liquidly sealed, wherein a sealing space isolated from the liquid and external air is formed in the housing by the housing body and the gas separation film, and the gas separation film penetrates the dissolved hydrogen gas in the liquid into the sealing space. In this case, the hydrogen sensor device may further include a pumping unit coupled to the housing by pumping oxygen in the sealing space to the outside to remove the oxygen.

The sensor unit may include a hetero-assembly of an oxygen ion conductor and a hydrogen ion conductor, a sensing electrode formed on the surface of the hydrogen ion conductor, a reference electrode formed on the surface of the oxygen ion conductor, and an electromotive force measuring unit measuring electromotive force between the reference electrode and the sensing electrode, and the sensing electrode is exposed to the sealing space, the reference electrode is in communication with the external air or is covered with a reference substance that fixes oxygen partial pressure at the reference electrode side, and as the concentration of the dissolved hydrogen gas is changed, the electromotive force is changed. Alternatively, the sensor unit may include a hydrogen ion conductor, a sensing electrode and a reference electrode formed on the surface of the hydrogen ion conductor, and an electromotive force measuring unit measuring the electromotive force between the reference electrode and the sensing electrode, and the sensing electrode may be exposed to the sealing space, the reference electrode may be covered with the reference substance that fixes hydrogen partial pressure at the reference electrode side, and as the concentration of the dissolved hydrogen gas is changed, the electromotive force may be changed.

The gas separation film may be a metallic film and the metallic film may include palladium (Pd) and have a thickness of 100 μm or less.

Further, the hydrogen sensor device according to one aspect of the present invention may further include a fixing cap for coupling the gas separation film to the housing and the sealing space in the housing may be filled with a filling material.

In addition, the hydrogen sensor device according to the present invention may include a heater for heating the sensor unit up to a sensing temperature.

The pumping unit for pumping oxygen in the sealing space to the outside may include an oxygen ion conductor, a heater substrate spaced apart from the oxygen ion conductor with a predetermined interval by a spacer, the spaced interval being provided to be in communication with the external air, a first pumping electrode formed on one surface of the oxygen ion conductor at the sealing space side, a second pumping electrode formed on one surface of the oxygen ion conductor at the external air side, and a pumping power supply applying voltage or current between the first pumping electrode and the second pumping electrode, and the voltage or current may be applied between the first pumping electrode and the second pumping electrode by the pumping power supply to pump oxygen at the sealing space side to the external air side.

The pumping unit may be integrally formed with the sensor unit and in this case, the sensor unit may include an oxygen ion conductor, a heater substrate spaced apart from the oxygen ion conductor with a predetermined interval by the spacer, the spaced interval being provided to be in communication with the external air, the hydrogen ion conductor attached to at least a part of the oxygen ion conductor exposed to the sealing space side, a sensing electrode formed on the surface exposed to the sealing space of the hydrogen ion conductor, a reference electrode formed on the surface of the oxygen ion conductor at the external air side, an electromotive force measuring unit measuring the electromotive force between the reference electrode and the sensing electrode, a first pumping electrode formed on the surface of the sealing space side which is not attached to the hydrogen ion conductor of the oxygen ion conductor, a second pumping electrode formed on the surface of the oxygen ion conductor at the external air side, and a pumping power supply applying the voltage between the first pumping electrode and the second pumping electrode, and as the concentration of the dissolved hydrogen gas is changed, the electromotive force is changed, and the voltage or current may be applied between the first pumping electrode and the second pumping electrode by the pumping power supply to pump the oxygen at the sealing space side to the external air side and herein, the reference electrode and the second pumping electrode may be one electrode.

Meanwhile, the hydrogen sensor device according to the present invention may be a hydrogen sensor device coupled to an opening portion of a container containing the liquid to measure the concentration of the dissolved hydrogen gas in the liquid contained in the container, and in this case, the gas separation film may be in communication with the inside of the container through the opening portion to penetrate the dissolved hydrogen gas in the liquid into the sealing space. In this case, while a sealing member is inserted between the gas separation film and the opening portion and between the housing body and the gas separation film, the hydrogen sensor device may be coupled to the opening portion and the hydrogen sensor device may further include at least one of a temperature sensor for measuring a temperature of the sensor unit and a liquid inflow sensor for sensing whether the liquid flows in.

According to another aspect of the present invention, a dissolved hydrogen measuring device for measuring a concentration of dissolved hydrogen gas in liquid contained in a container includes: a hydrogen sensor device coupled to an opening portion provided at one side of the container, wherein the hydrogen sensor device includes a sensor unit measuring a concentration of hydrogen gas; and a housing coupled to the sensor unit, the housing including a housing body having an opening portion formed in at least a part thereof and a gas separation film coupled to the opening portion to be gaseously and liquidly sealed to have a sealing space isolated from the liquid and external air therein, and the gas separation film is in communication with the inside of the container through the opening portion to penetrate the dissolved hydrogen gas in the liquid into the sealing space. The hydrogen sensor device may be coupled to the opening portion to be attached/detached.

Further, the dissolved hydrogen measuring device may further include a control device electrically connected to the sensor unit to control an operation of the sensor unit and may further include a temperature sensor for measuring a temperature of the sensor unit or a liquid inflow sensor for sensing whether the liquid flows in, and the control device may receive a sensing result from the temperature sensor or the liquid inflow sensor. In addition, an opening/closing valve may be installed in the opening portion, and the control device may be configured to control an operation of the opening/closing valve.

The control device may include a measurement unit receiving a measurement result from the sensor unit, a control unit controlling an operation of the hydrogen sensor device, a display unit displaying the measured concentration of the dissolved hydrogen gas, and a transmission unit transmitting a result of the measurement of the concentration of the dissolved hydrogen gas by a wired or wireless method. Herein, the hydrogen sensor device may further include a pumping unit pumping oxygen in the sealing space to the outside to remove the oxygen and the pumping unit may be configured to include an oxygen ion conductor, a first pumping electrode formed on one surface of the oxygen ion conductor at the sealing space side and a second pumping electrode formed on one surface of the oxygen ion conductor at the external air side, and the control unit may be configured to control an operation of the pumping unit.

Further, the pumping unit may measure electromotive force between the first pumping electrode and the second pumping electrode to perform even an oxygen sensor function to measure partial pressure of oxygen gas in the sealing space, and the control unit may be configured to receive a result of measuring the partial pressure of the oxygen gas in the sealing space from the pumping unit that performs the oxygen sensor function and thereafter, control a pumping operation of the pumping unit based on the result.

A method for measuring a concentration of dissolved hydrogen gas in liquid by using a dissolved hydrogen measuring device according to another aspect of the present invention includes: measuring a temperature of a sensor unit by using a temperature sensor; controlling the temperature of the sensor unit to become the measurement temperature based on a result of the temperature measurement; and measuring partial pressure of hydrogen gas in a sealing space by using the sensor unit and calculating the concentration of the dissolved hydrogen gas by using a result of the measurement. In this case, the hydrogen sensor device may further include a pumping unit pumping oxygen in the sealing space to the outside to remove the oxygen, the pumping unit may be configured to include an oxygen ion conductor, a first pumping electrode formed on one surface of the oxygen ion conductor at the sealing space side and a second pumping electrode formed on an external surface of the oxygen ion conductor, and the pumping unit may measure electromotive force between the first pumping electrode and the second pumping electrode to perform even an oxygen sensor function to measure partial pressure of oxygen gas in the sealing space, and the pumping unit performing the oxygen sensor function may perform measuring partial pressure of oxygen gas in the sealing space to determining whether the measured partial pressure of the oxygen gas is equal to or higher than a reference value, controlling the pumping operation of the pumping unit so as to discharge the oxygen gas in the sealing space to the outside when the measured partial pressure of the oxygen gas is equal to or higher than the reference value according to a result of the determination, and measuring the partial pressure of the hydrogen gas when the measured partial pressure of the oxygen gas is equal to or lower than the reference value.

Further, the method may further include transmitting the measured and calculated concentration of the dissolved hydrogen gas by a wired or wireless method and the hydrogen sensor device may further include a liquid inflow sensor for sensing whether the liquid flows in and the method may further include announcing, when it is determined that the liquid flows in by receiving the sensing result from the liquid inflow sensor, the inflow of the liquid.

According to yet another aspect of the present invention, a hydrogen sensor device for measuring a concentration of dissolved hydrogen gas in liquid includes: a housing having a cylindrical shape in which at least a partial area is opened and a gas separation film is coupled to the opened partial area, the gas separation film being not capable of penetrating the liquid but capable of penetrating hydrogen gas; and a sensor unit including at least a first electrode and a second electrode, wherein the sensor unit is coupled to the housing so that the first electrode is inserted into the housing to measure a concentration of hydrogen gas that enters the housing through the gas separation film to contact the first electrode.

According to still yet another aspect of the present invention, a hydrogen sensor device at least partially inserted into liquid to measure a concentration of dissolved hydrogen gas in the liquid includes: a sensing unit including a reference electrode and a sensing electrode at both sides of a solid electrolyte; a reference gas passage for supplying reference gas to the reference electrode while being isolated from the liquid; a heater unit for heating the sensor unit up to a sensing temperature; and an electromotive force measuring unit measuring electromotive force between the reference electrode and the sensing electrode, wherein the sensing electrode is exposed to the dissolved hydrogen gas in the liquid and as the concentration of the dissolved hydrogen gas is changed, the electromotive force is changed. Herein, instead of the reference gas passage for supplying reference gas to a reference electrode, a reference gas partial pressure fixing reference substance covering the reference electrode to fix reference gas partial pressure at the reference electrode side may be provided.

The solid electrolyte may be formed by hetero junction of an oxygen ion conductor and a hydrogen ion conductor or the hydrogen ion conductor, and the sensing electrode may be formed on the surface of the hydrogen ion conductor.

Further, the hydrogen sensor device may further include a protecting material formed to at least cover the sensing electrode and the protecting material may be formed by a porous material or glass ceramic through which hydrogen gas is capable of passing.

Advantageous Effects

A hydrogen sensor device according to the present invention can simply measure a concentration of dissolved hydrogen gas in liquid in real time without high-priced equipment.

Further, the hydrogen sensor device includes a housing to be exposed to dissolved hydrogen gas while isolating at least a sensing electrode of a hydrogen sensor from the liquid, and as a result, a problem is reduced, in which the hydrogen sensor, in particular, a sensing electrode of the hydrogen sensor deteriorates by the liquid.

In addition, the hydrogen sensor device according to the present invention includes a pumping unit that discharges interfering gas which is present in the housing to the outside to minimize an influence of other gases including oxygen gas, and the like in measuring the concentration of the dissolved hydrogen gas.

Moreover, by the hydrogen sensor device and a method for measuring a concentration of hydrogen gas according to the present invention, accuracy and reproducibility of measurement can be secured and a user can know a measurement result even from a long distance.

DESCRIPTION OF DRAWINGS

FIG. 3 is an exploded perspective view of the sensor unit of FIG. 2.

BEST MODE

Figure 1:
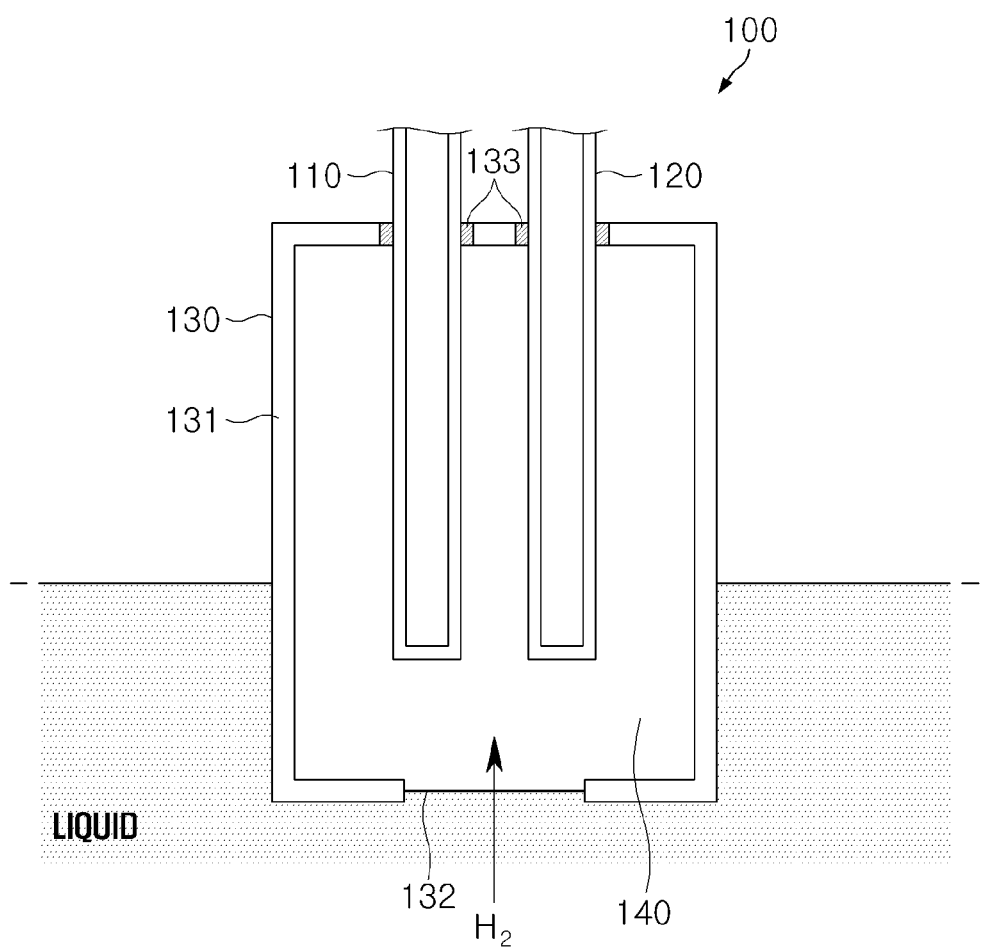
FIG. 1 is a schematic cross-sectional view of a hydrogen sensor device according to a first embodiment of the present invention.

Hereinafter, embodiments of the present invention will be described in detail with reference to the accompanying drawings, but the present invention is not limited or restricted to the embodiments. In describing various embodiments of the present invention, corresponding components are described with the same names and the same reference numerals.

FIG. 1 is a schematic cross-sectional view of a hydrogen sensor device 100 according to a first embodiment of the present invention. Referring to FIG. 1, the hydrogen sensor device 100 according to the first embodiment of the present invention may be configured to include a sensor unit 110 and a housing 130 and configured to selectively further include a pumping unit 120. Herein, the sensor unit 110 is a component corresponding to a hydrogen sensor for measuring a concentration of ambient hydrogen gas and the housing 130 is a component for forming a sealing space 140 for isolating one end of the sensor unit 110 from liquid and external air. Even when the hydrogen sensor device 100 is inserted into the liquid, the sensor unit 110 is isolated from the liquid by the housing 130, but dissolved hydrogen gas penetrates into the sealing space 140 through a gas separation film 132 provided in at least a part inserted into the liquid of the housing 130, and as a result, the sensor unit 110 may measure the concentration of the dissolved hydrogen gas without directly contacting the liquid. Hereinafter, each component of the hydrogen sensor device 100 according to the first embodiment of the present invention will be described in detail.

The sensor unit 110 as a component corresponding to a hydrogen sensor for measuring the concentration of the hydrogen gas in the sealing space 140 and the sensor unit 110 is particularly to the hydrogen sensor that may measure the concentration of the hydrogen gas, but the sensor unit 110 is preferably a solid electrolyte hydrogen sensor. A preferable structure of the sensor unit according to the first embodiment of the present invention will be described with reference to a schematic cross-sectional view of FIG. 2.

Figure 2:
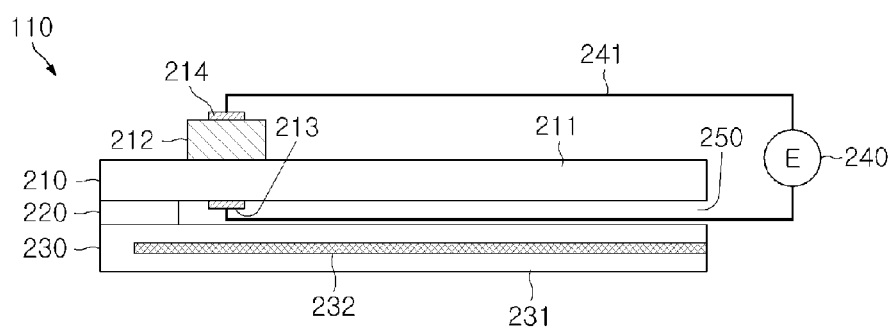
FIG. 2 is a schematic cross-sectional view of a sensor unit according to the first embodiment of the present invention.

As illustrated in FIG. 2, the sensor unit 110 may include a sensing unit 210 including an oxygen ion conductor 211, a hydrogen ion conductor 212 attached to one surface of the oxygen ion conductor 211, a reference electrode 213 formed on the other surface of the oxygen ion conductor 211, that is, at a reference gas passage 250, and a sensing electrode 214 formed on the surface of the hydrogen ion conductor 212, a heater unit 230 for heating the sensing unit 210 at a predetermined temperature, and a spacer 220 spacing the sensing unit 210 and the heater unit 230 apart by a predetermined interval and forming the reference gas passage 250 therebetween. The reference electrode 213 and the sensing electrode 214 are electrically connected to an electromotive force measuring unit 240 through a lead wire 241 to measure the concentration of the hydrogen gas according to a principle to be described below by measurement of electromotive force.

As the oxygen ion conductor 211, $CeO_2$ based compounds prepared by adding solid electrolyte or $Gd_2O_3$ may be used, such as stabilized zirconia prepared by adding various substances to zirconia ($ZrO_2$), for example, Yttria stabilized zirconia (YSZ), calcium stabilized zirconia (CSZ), and magnesium stabilized zirconia (MSZ) and as the hydrogen ion conductor 212, substances acquired by substituting a B position of a substance having an $ABO_3$ type perovskite structure with various substances, for example, $CaZrO_3$ based compounds including $CaZr_{0.9}In_{0.1}O_{3-x}$, and the like, $SrZrO3$ based compounds including $SrZr_{0.95}Y_{0.05}O_{3-x}$, and the like, based compounds including and the like, $BaCeO_3$ based compounds including $BaCe_{0.9}Nd_{0.1}O_{3-x}$, and the like, and Ti based compounds including $BaTiO_3$, $SrTiO_3$, $PbTiO_3$, and the like may be used.

Further, the reference electrode 213 and the sensing electrode 214 are preferably made of precious metal such as platinum (Pt), or the like.

The spacer 220 as a component inserted between the sensing unit 210 and the heater unit 230 to form the reference gas passage 250 so that the reference electrode 213 is in communication with reference gas may be made of alumina. In this case, the reference gas is not particularly limited to gas in which oxygen partial pressure is substantially constantly maintained, but the reference gas is preferably external air.

The heater unit 230 as a component for heating the sensing unit 210 up to a sensing temperature may be a form in which a heater wire 232 is formed on a heater substrate 231 made of an insulating substance such as alumina, or the like. Herein, the heater wire 232 may be a platinum (Pt) wire and although not illustrated, may further include a power supply unit for making current flow on the heater wire 232. Further, when the heater wire 232 is exposed to the outside, electric resistance varies and temperature reproducibility deteriorates, and as a result, it is preferable that the heater wire 232 is incorporated in the heater substrate 231 to be blocked from the outside.

Figure 3A:
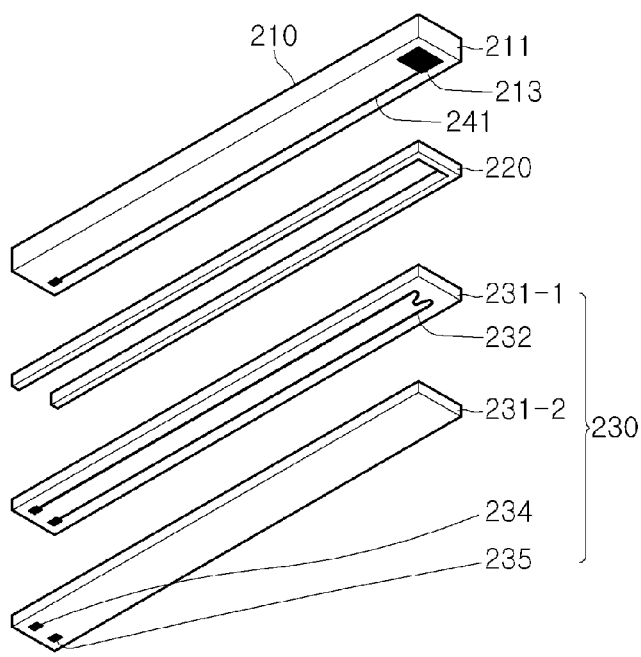
FIG. 3(a) is a perspective view viewed from the bottom.
Figure 3B:
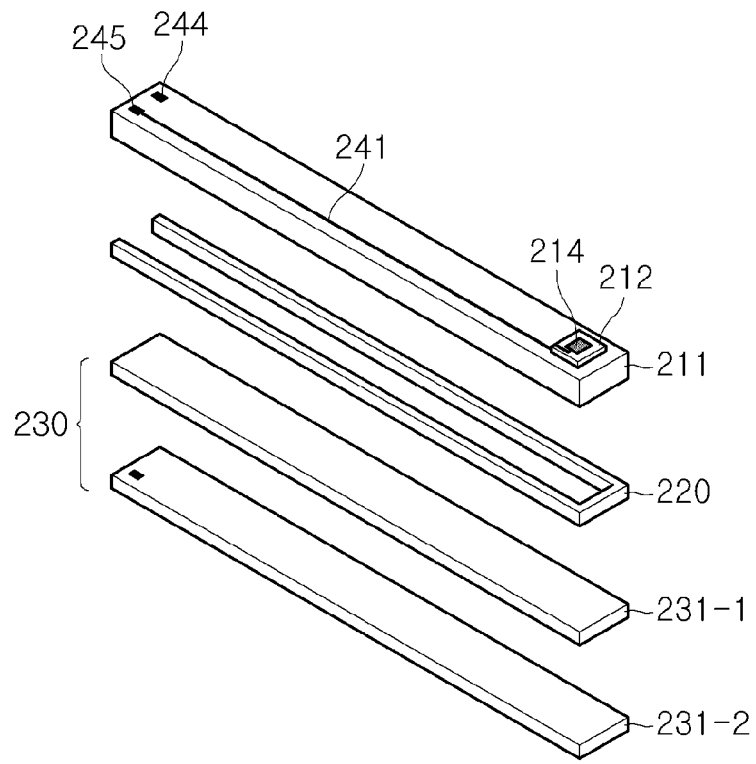
FIG. 3(b) is a perspective view viewed from the top.

FIG. 3 is an exploded perspective view of the sensor unit 110 of FIG. 2, FIG. 3(a) is a perspective view viewed from the bottom, and FIG. 3(b) is a perspective view viewed from the top.

Referring to FIG. 3, the oxygen ion conductor 211 is formed by a rectangular thin plate and the hydrogen ion conductor 212 is thus attached onto the top of one end positioned in an internal sealing space 140 of the housing 130 and the sensing electrode 214 is formed on the top thereof and the reference electrode 213 is formed at a position facing the hydrogen ion conductor 212 and the sensing electrode 214 on the bottom thereof. The lead wire 241 extends to the other end from each of the reference electrode 213 and the sensing electrode 214 to form a pair of sensor terminals 244 and 245 connected with the electromotive force measuring unit 240. In this case, the reference electrode 213 and the lead wire 241 that extends from the reference electrode 213 are formed on the bottom of the oxygen ion conductor 211, but a through-hole is formed in the oxygen ion conductor 211 and filled with a conductive substance, and as a result, as illustrated in FIG. 3, the sensor terminal 244 connected with the lead wire 241 which extends from the reference electrode 213 may be formed on the top of the oxygen ion conductor 211 and such a configuration is applied to further facilitate connection with the electromotive force measuring unit 240. Further, in FIG. 3, the oxygen ion conductor 211 is illustrated as one plate member, but may have a form in which a plurality of thin plate members overlap with each other.

The spacer 220 has a '⌐' shape to form the reference gas passage 250 of which one side is opened between the sensing unit 210 and the heater unit 230. Since the reference gas passage 250 is a part which is in communication with the external air even though the hydrogen sensor device 100 is inserted into the liquid as illustrated in FIG. 1, the reference electrode 213 is in contact with the reference gas, that is, the external air through the reference gas passage 250 while being isolated from the hydrogen gas in the sealing space 140.

The heater unit 230 includes a heater upper substrate 231-1, a heater wire 232 formed on the bottom of the heater upper substrate 231-1, and a heater lower substrate 231-2 covering the heater upper substrate 231-1 so as to prevent the heater wire 232 from being exposed to the outside and the heater wire 232 may be formed on not the bottom of the heater upper substrate 231-1 but the top of the heater lower substrate 231-2. The heater wire 232 may be formed by printing the platinum (Pt) on the heater upper substrate 231-1 or the heater lower substrate 231-2 with a predetermined pattern and since a heater structure using a platinum pattern is well known in a gas sensor field, detailed description thereof will be omitted. Meanwhile, for connection easiness of a power supply that supplies current to the heater wire 232, the through-hole is formed in the heater lower substrate 231-2 and filled with the conductive substance, and as a result, a pair of heater terminals 234 and 235 connected with the heater wire 232 are preferably formed on the bottom of the heater lower substrate 231-2.

The sensor unit 110 illustrated in FIGS. 2 and 3 has a quadrangular cylindrical shape when the sensing unit 210, the spacer 220, and the heater unit 230 are integrally coupled with each other and this may be manufactured by using a tape casting technology. Further, in FIGS. 2 and 3, it is described that the sensing unit 210, the spacer 220, and the heater unit 230 are separate components, but the sensor unit 110 having a packaging body shape, in which the respective components are integrally coupled with each other may be manufactured by using a manufacturing technology such as ceramic extrusion, or the like and in this case, since the spacer 220 and the heater unit 230 are also made of an oxygen ion conductor substance such as YSZ, or the like, when the heater wire 232 is incorporated in the heater unit 230, the heater wire 232 is preferably incorporated after the heater wire 232 is subjected to the surface of the insulating film processing so that the heater wire 232 becomes in an electrical insulating state with the oxygen ion conductor. Alternatively, a structure may also be used, in which a separate heater unit is provided to be inserted and installed in the reference gas passage 250 or installed to be close to an external surface of the sensor unit 110.

Figure 4:
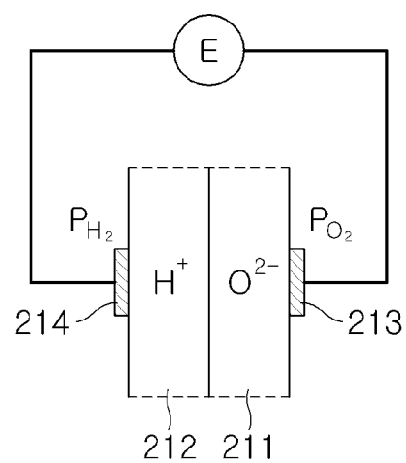
FIG. 4 is a diagram for describing a principle in which the sensor unit of FIGS. 2 and 3 senses a concentration of hydrogen gas.

A principle in which the sensor unit 110 illustrated in FIGS. 2 and 3 senses the concentration of the hydrogen gas will be described by using FIG. 4. FIG. 4 is a diagram acquired by enlarging only a part in which the sensing electrode 214 and the reference electrode 213 of the sensing unit 210 are formed in the sensor unit 110 of FIGS. 2 and 3 and FIG. 4 illustrates a structure of a solid electro-chemical cell in which the oxygen ion conductor 211 and the hydrogen ion conductor 212 are hetero-joined. In the solid electro-chemical cell having such a structure, electromotive force E measured between the reference electrode 213 and the sensing electrode 214 establishes the following relationship with oxygen partial pressure $P_{O2}$ at the reference electrode 213 side and hydrogen partial pressure $P_{H2}$ at the sensing electrode 214 side.

$$E = Eo + A \log P_{H2} + (A/2) \log P_{O2} \quad (1)$$

Since Eo and A are constants that depend on only a temperature in the equation, consequently, when the oxygen partial pressure $P_{O2}$ at the reference electrode 213 side is known, it can be seen that the hydrogen partial pressure $P_{H2}$ at the sensing electrode 214 side may be decided by measuring the electromotive force E.

In this case, since the reference electrode 213 is isolated from the liquid and the hydrogen gas in the sealing space 140 and is thus in communication with the external air through the reference gas passage 250, the oxygen partial pressure $P_{O2}$ at the reference electrode 213 side is fixed to 0.21 atmospheric pressure which is the oxygen partial pressure in the air. Therefore, when the electromotive force E is measured in Equation (1), the oxygen partial pressure $P_{H2}$ at the sensing electrode 214 side may be calculated.

Herein, since the hydrogen partial pressure $P_{H2}$ at the sensing electrode 214 side is partial pressure of the hydrogen gas which is present in the sealing space 140 by passing through the gas separation film 132 and the partial pressure of the hydrogen gas in the sealing space 140 and the concentration of the dissolved hydrogen gas in the liquid are in proportion to each other in a thermodynamic balance state, when a proportional relation equation or data is experimentally deduced in advance to be made into database, the concentration of the dissolved hydrogen gas in the liquid may be calculated by measuring the partial pressure of the hydrogen gas in the sealing space 140. Further, the proportional relation equation between the partial pressure of the hydrogen gas in the sealing space 140 and the concentration of the dissolved hydrogen gas in the liquid may be theoretically deduced and since the amount of hydrogen dissolved in the liquid is in proportion to a square root of evaporated hydrogen partial pressure according to a Sievert rule, the concentration of the dissolved hydrogen gas in the liquid may be calculated from the concentration of the hydrogen gas, which is measured by the hydrogen sensor device 100 by using the rule.

Since a temperature of the sensing unit 210 is preferably approximately 500° C. or higher at the time of measuring the concentration of the hydrogen gas, predetermined current is applied to the heater wire 232, and as a result, the sensing unit 110 is heated at a corresponding temperature and thereafter, it is preferable to measure the electromotive force between the reference electrode 213 and the sensing electrode 214 by the electromotive force measuring unit 240.

Figure 5:
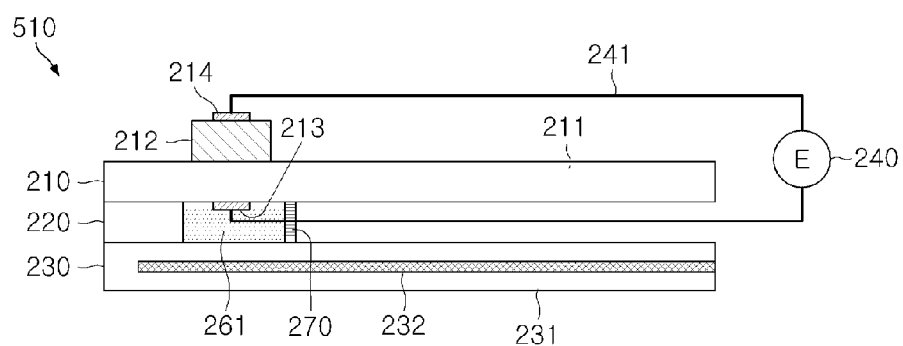
FIG. 5 is a schematic cross-sectional view of a sensor unit having another structure, which may be used by the hydrogen sensor device according to the first embodiment of the present invention.

FIG. 5 is a schematic cross-sectional view for describing another structure of a sensor unit which may be used by the hydrogen sensor device 100 according to the first embodiment of the present invention. In this case, description of contents common to the description referring to FIGS. 1 to 4 is omitted, but it should be appreciated that the contents may be similarly applied even to the sensor unit of FIG. 5 and the hydrogen sensor device 100 including the same.

According to FIG. 5, the sensor unit 510 having another structure, which may be used in the first embodiment of the present invention is different from the sensor unit 110 of FIGS. 2 and 3 in terms of a structure in which the reference electrode 213 is covered with an oxygen partial pressure fixing reference substance 261 and the top thereof is sealed with a sealing cover 270 instead of exposing the reference electrode 213 to the reference gas passage to directly contact the external air.

As the oxygen partial pressure fixing reference substance 261, mixtures of metal and metal oxides, such as Cu/CuO, Ni/NiO, Ti/TiO$_2$, Fe/FeO, Cr/Cr$_2$O$_3$, Mo/MoO, and the like or mixtures of metal oxides having different oxidation degrees, such as Cu$_2$O/CuO, FeO/Fe$_2$O$_3$, and the like may be used and when the reference electrode 213 is covered with the oxygen partial pressure fixing reference substance 261, the oxygen partial pressure at the reference electrode 213 side may be thermodynamically fixed. That is, the oxygen partial pressure at the reference electrode 213 side is decided by the oxygen partial pressure fixing reference substance 261 instead of the external air and similarly to the description referring to FIG. 4, the concentration of the dissolved hydrogen gas in oil may be decided by Equation (1) by measuring the electromotive force between the reference electrode 213 and the sensing electrode 214.

The sealing cover 270 as a component for preventing the external air from influencing the reference electrode 213 through the oxygen partial pressure fixing reference substance 261 may be made of a dense ceramic substance capable of preventing penetration of the air, and the like. If the sealing cover 270 is slightly influenced by the external air, the sealing cover 270 may be omitted.

Figure 6:
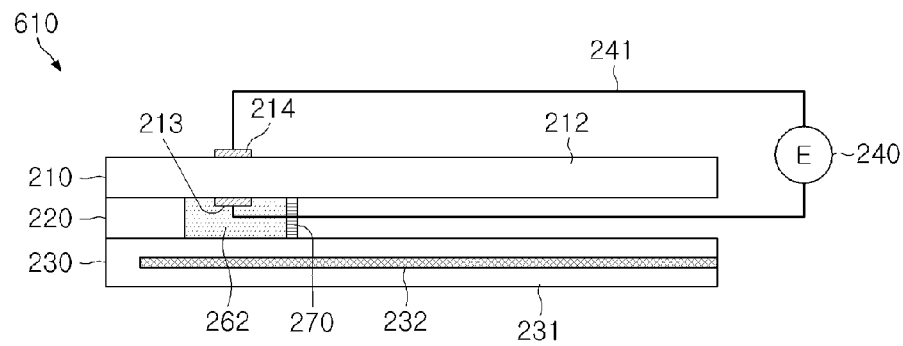
FIG. 6 is a schematic cross-sectional view of a sensor unit having yet another structure, which may be used by the hydrogen sensor device according to the first embodiment of the present invention.

FIG. 6 is a schematic cross-sectional view for describing yet another structure of a sensor unit which may be used by the hydrogen sensor device 100 according to the first embodiment of the present invention. In this case, description of contents common to the description referring to FIGS. 1 to 5 is omitted, but it should be appreciated that the contents may be similarly applied to the sensor unit of FIG. 6 and the hydrogen sensor device 100 including the same.

According to FIG. 6, in the sensor unit 610 having yet another structure, which may be used in the first embodiment of the present invention, the sensing unit is formed by only the hydrogen ion conductor instead of the hetero junction of the oxygen ion conductor and the hydrogen ion conductor. That is, the sensing electrode 214 is formed at one side of the hydrogen ion conductor 212 and the reference electrode 213 is formed at the other side, and the reference electrode 213 is covered with a hydrogen partial pressure fixing reference substance 262 and the top of the hydrogen partial pressure fixing reference substance 262 is sealed with the sealing cover 270.

As the hydrogen partial pressure fixing reference substance 262, mixed phases of metal and metal hydrides, such as Ti/TiH$_2$, Zr/ZrH$_2$, Ca/CaH$_2$, Nd/NdH$_2$, and the like may be used and the hydro partial pressure P$^2_{H2}$ at the reference electrode 213 side may be thermodynamically fixed by the mixed phases.

Since the sensing electrode 214 contacts the hydrogen gas in the sealing space 140 formed by the housing 130, when the electromotive force E between the sensing electrode 214 and the reference electrode 213 is measured, the partial pressure of the hydrogen gas in the sealing space 140 may be measured by a well-known Nernst equation given below and the partial pressure P$^1_{H2}$ of the dissolved hydrogen gas in the liquid may be calculated therefrom.

$$E = -\frac{RT}{2F}\ln\frac{P^1_{H2}}{P^2_{H2}} \quad (2)$$

In Equation (2) given above, R represents a gas constant, F represents a Faraday constant, and T represents a measured temperature and all of R, F, and T are constants and since the hydrogen partial pressure P$^2_{H2}$ of the reference electrode 213 side is also a value decided by the hydrogen partial pressure fixing reference substance 262, the partial pressure P$^1_{H2}$ of the dissolved hydrogen gas in the liquid may be decided from the measured electromotive force E value.

Hereinabove, it has been described that the sensor units 110, 510, and 610 described as the example have the structure in which the reference electrode 213 is isolated from the hydrogen gas in the sealing space 140 by the sensing unit 210, the spacer 220, and the heater unit 230 to contact the reference gas passage 250 or the reference substances 261 and 262, but the sensor units having such a structure should not particularly be used in order to implement technical spirit of the present invention and various sensor unit structures may be used. As an example, a separate handle unit may be provided, which is connected to the oxygen ion conductor or the hydrogen ion conductor to be gaseously sealed and modified examples will be described in brief with reference to FIGS. 7 to 9.

Figure 7:
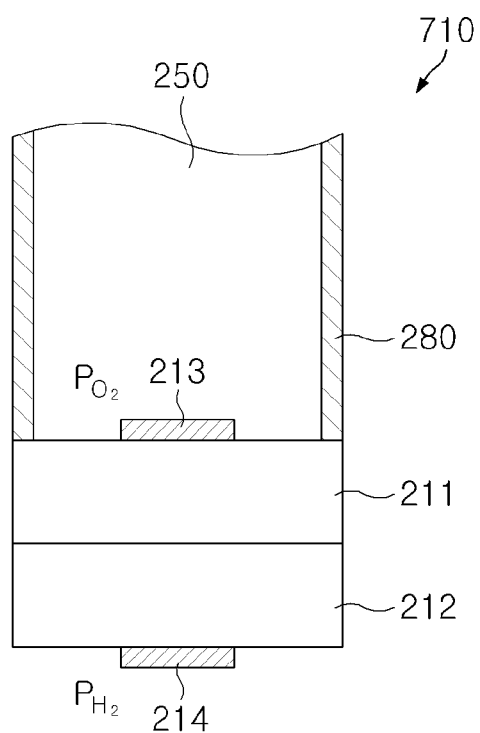
FIG. 7 is a modified example of the sensor unit illustrated in FIG. 2.

FIG. 7 illustrates a modified example of the sensor unit 110 of FIG. 2 and the oxygen ion conductor 211 and the hydrogen ion conductor 212 are each formed in a circular or polygonal pellet form to be attached to each other and the reference electrode 213 and the sensing electrode 214 are formed on the surface of each conductor. In addition, a separate handle unit 280 is provided to be coupled to the oxygen ion conductor 211 to be gaseously sealed and the handle unit 280 may have a hollow tube shape which is in communication with the external air. When the housing 130 is coupled to the sensor unit 710 having such a configuration so that the sensing electrode 214 is at least included in the sealing space 140, the sensing electrode 214 contacts the hydrogen gas in the sealing space 140 and the reference electrode 213 is positioned in the reference gas passage 250 while being isolated from the dissolved hydrogen gas to contact the external air similarly to the case in which the sensor unit 110 according to FIG. 2 is used, and as a result, the concentration of the dissolved hydrogen gas in the liquid may be measured according to the aforementioned principle. The heater unit is not illustrated in FIG. 7, but the heater unit may be installed at an appropriate location adjacent to the oxygen ion conductor or the hydrogen ion conductor, such as the reference gas passage 250, or the like.

Figure 8:
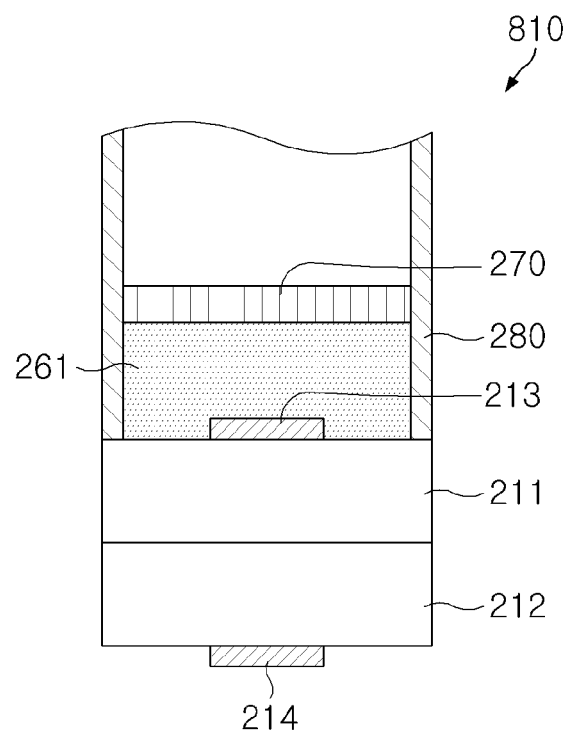
FIG. 8 is a modified example of the sensor unit illustrated in FIG. 5.

FIG. 8 as a modified example of the sensor unit 510 of FIG. 5 is different from the sensor unit 710 of FIG. 7 in terms of a structure in which the reference electrode 213 is covered with the oxygen partial pressure fixing reference substance 261 and the top thereof is sealed with the sealing cover 270 instead of exposing the reference electrode 213 to the reference gas passage to directly contact the external air. The sensor unit of FIG. 8 is similar to the sensor unit 510 of FIG. 5 in that when the reference electrode 213 is covered with the oxygen partial pressure fixing reference substance 261, the oxygen partial pressure of the reference electrode 213 side may be thermodynamically fixed, and therefore, the concentration of the dissolved hydrogen gas in the liquid may be decided by measuring the electromotive force between the reference electrode 213 and the sensing electrode 214. The heater unit is not illustrated in FIG. 8, but the heater unit may be installed at an appropriate location adjacent to the oxygen ion conductor or the hydrogen ion conductor, such as the inside of the handle unit 280, or the like.

Figure 9:
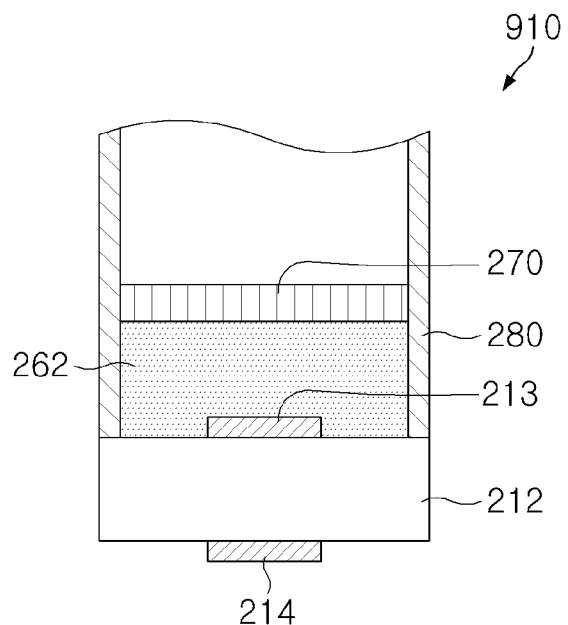
FIG. 9 is a modified example of the sensor unit illustrated in FIG. 6.

FIG. 9 as a modified example of the sensor unit 610 of FIG. 6 illustrates a structure in which the reference electrode 213 and the sensing electrode 214 are formed on both surfaces of the hydrogen ion conductor 212 having the circular or polygonal pellet form, and the reference electrode 213 is covered with the hydrogen partial pressure fixing reference substance 262 and the top thereof is sealed with the sealing cover 270 and herein, the separate handle unit 280 is coupled to the hydrogen ion conductor 212 to be gaseously sealed. According to the hydrogen sensor device having such a configuration, since the hydrogen partial pressure of the reference electrode 213 side is fixed by the hydrogen partial pressure fixing reference substance 262, the concentration of the hydrogen gas in the sealing space 140 may be measured by Equation (2) similarly to the sensor unit 610 of FIG. 6. The heater unit is not illustrated in FIG. 9, but the heater unit may be installed at the appropriate location adjacent to the hydrogen ion conductor, such as the inside of the handle unit 280, or the like.

Referring back to FIG. 1, the housing 130 according to the first embodiment of the present invention will be described in detail. The housing 130 as a component for forming the sealing space 140 that isolates one end of the sensor unit 110 from the liquid and the external air is configured to include a housing body 131 in which the inside is empty and at least a part of each of both ends is opened and a gas separation film 132 coupled to one end of a direction in which the housing body 131 is inserted into the liquid to prevent the liquid from penetrating into the sealing space 140 and selectively penetrating the dissolved hydrogen gas in the liquid. The housing body 131 is not particularly limited to a material which the liquid and gas may not penetrate and may be made of, for example, a glass material. Glass is a material which the hydrogen gas may penetrate through diffusion, but the housing body is much thicker than the gas separation film 132, and as a result, gas penetration into the sealing space 140 through the housing body 131 is substantially disregardable.

The gas separation film 132 as a component coupled to an opened area of one end of the housing body 131 to penetrate the dissolved hydrogen gas in the liquid into the sealing space 140 is not particularly limited to a material which the liquid may not pass through and dissolved gas molecules may pass through, but a polymer material such as a poly tetra fluoro ethylene (PTFE) membrane or a polydimethylsiloxane (PDMS) membrane, a porous ceramic material, or a metal foil may be used.

In particular, since the partial pressure of the hydrogen gas in the sealing space 140 needs to reach a balance state within a short time for a rapid reaction time of the hydrogen sensor device 100, the gas separation film 132 is preferably made of a material which may have a large diffusion coefficient of hydrogen and a foil form having a small thickness. That is, when a diffusion speed of the hydrogen through the gas separation film 132 is low, since a time required until the concentration of the hydrogen gas in the sealing space 140 establishes a balance with the concentration of the dissolved hydrogen gas in the liquid is long, tens of minutes or longer may be required for accurately measuring the concentration of the dissolved hydrogen gas in the liquid by using the hydrogen sensor device 100 according to the present invention and this may not completely meet an object of the present invention to conveniently measure the concentration of the dissolved hydrogen gas in the liquid in real time.

A diffusion distance x of the hydrogen through the gas separation film 132 is expressed by an equation (3) given below.

$$x=2(Dt)^{1/2} \quad (3)$$

Where, D represents a diffusion coefficient of the hydrogen in the gas separation film 132 and t represents a diffusion time. That is, according to the equation (3), it can be seen that as the diffusion coefficient D is larger and the diffusion time t increases the diffusion distance x of the hydrogen gas increases and it can be seen that it is preferable to reduce the thickness of the gas separation film 132 and form the gas separation film with a material of which the diffusion coefficient D is large in order to reduce the diffusion time t so that the partial pressure of the hydrogen gas in the sealing space 140 reaches the balance with the concentration of the dissolved hydrogen gas in the liquid within the short time.

Based on such a principle, the metal foil is more preferable than a material such as glass or plastic of which thickness is difficult to decrease, as the gas separation film 132 of the present invention. The metal foil, in particular, a palladium alloy is large in hydrogen diffusion coefficient as a level of $10^{-6}$ cm/s$^2$ and may be made in a thin foil form of 100 μm or less, and as a result, the palladium alloy is appropriate as the gas separation film 132 to be applied to the hydrogen sensor device 100 according to the present invention.

In FIG. 1, it is illustrated that the gas separation film 132 is coupled on the bottom of the housing body 131, but a coupling location may be modified and the gas separation film 132 may be coupled to for example, the side of the housing body 131.

Figure 10:
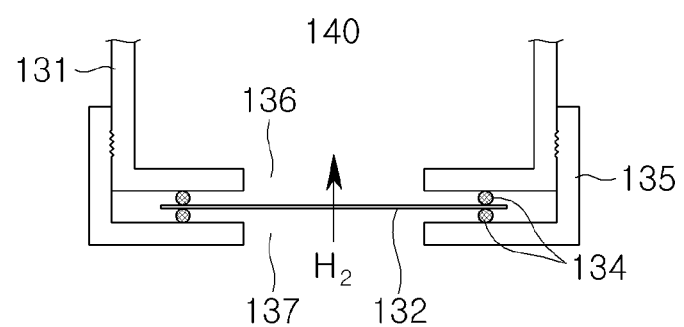
FIG. 10 is a diagram illustrating one example of a coupling method of a gas separation film.

As a method that couples the gas separation film 132 to the housing body 131, various methods may be used and for example, as illustrated in FIG. 10, a method using a fixing cap 135 coupled to the housing body 131 with the gas separation film 132 may be used. In this case, opening portions 136 and 137 are formed in both the housing body 131 and the fixing cap 135 in a part to which the gas separation film 132 is fixed and the dissolved hydrogen gas is configured to penetrate into the sealing space 140 and a sealing material 134 such as an O-ring, or the like is inserted between the housing body 131 and the gas separation film 132 and between the fixing cap 135 and the gas separation film 132 to be sealed so that the hydrogen gas passes through only the gas separation film 132. Further, a thread is formed in the fixing cap 135 and a packaging body 131 to be screw-fastened to the fixing cap 135 and the packaging body 131, but various other coupling methods may be used.

A part of the sensor unit 110 of the hydrogen sensor device 100 according to the present invention may be drawn to the outside of the housing 130 so that the reference gas passage 250 is in communication with the external air or for electrical connection with the electromotive force measuring unit 240 or a power supply for a heater even when the reference substances 261 and 262 are used instead of the reference gas passage 250 and in this case, a sealing member 133 is provided between the sensor unit 110 and the housing body 131, and as a result, the entirety of the housing 130 except for the gas separation film 132 is preferably in a gas sealing state. In this case, as the sealing member 133, glass frit may be used.

Meanwhile, when interfering gas influencing measurement of the concentration the hydrogen gas is present in the sealing space 140 except for the hydrogen gas, it may be difficult to guarantee accuracy of the measurement. In particular, when gas which is reactive to the hydrogen gas, for example, oxygen gas is present, the oxygen gas reacts with the hydrogen gas that enters the sealing space 140 through the gas separation film 132 to make vapor and decrease the hydrogen partial pressure, thereby interfering accurate measurement of the concentration of the dissolved hydrogen gas in the liquid. Accordingly, the hydrogen sensor device 100 according to the present invention may include a pumping unit 120 that may selectively discharge the interfering gas that exists in the sealing space 140 to the outside.

Figure 11:
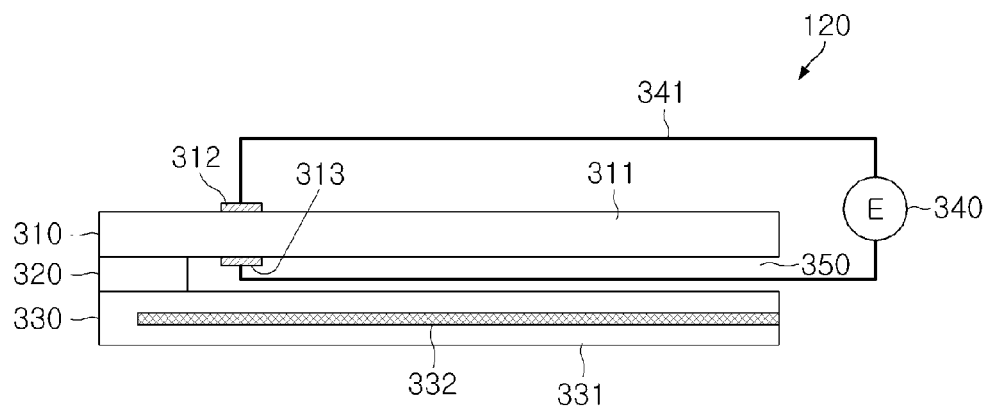
FIG. 11 is a schematic cross-sectional view of a pumping unit which can discharge hydrogen gas in a sealing space to the outside.

FIG. 11 is a schematic cross-sectional view for describing a preferable structure of a pumping unit 120 which can discharge oxygen gas in a sealing space 140 to the outside. Hereinafter, a structure of the pumping unit 120 is described with reference to FIG. 11, but the structure of the pumping unit 120 according to the present invention is not limited thereto.

The pumping unit 120 is configured to include a pumping cell 310, a spacer 320, and a pumping cell heating unit 330. The pumping cell 310 is a structure in which a first pumping electrode 312 and a second pumping electrode 313 are formed on both ends of the oxygen ion conductor 311 and when predetermined voltage or current is applied between the first and second pumping electrodes 312 and 313 from a pumping power supply 340 so that the second pumping electrode 313 becomes a positive (+) electrode, oxygen gas at the first pumping electrode 312 side moves through the oxygen ion conductor 311 to move to the second pumping electrode 313 side.

In this case, the pumping cell 310 needs to be heated at a predetermined temperature for a smooth operation and the pumping cell heating unit 330 is a component for the heating. The pumping cell heating unit 330 is spaced apart from the pumping cell 310 with a predetermined distance by the spacer 320 to form an oxygen discharge space 350 which is in communication with the external air and the pumping cell heating unit 330 and the spacer 320 may use the same configuration as the heating unit 230 and the spacer 220 provided in the sensor unit 110 of FIG. 2.

In the pumping unit 120 of FIG. 11, the first pumping electrode 312 is positioned in the sealing space 140 and the second pumping electrode 313 is coupled to the housing body 131 of the housing 130 to be in communication with the external air through an oxygen discharge space 350 and in this case, a coupling portion thereof may be sealed by the sealing member 133. When predetermined voltage or current is applied between the first and second pumping electrodes 312 and 313 from the pumping power supply 340 so that the second pumping electrode 313 becomes the positive (+) electrode in such a coupling state, oxygen gas that is present in the first pumping electrode 312 side, that is, the sealing space 140 is discharged to the outside through the oxygen discharge space 350. In this case, the oxygen partial pressure in the sealing space 140 may be predicted by the Nernst equation and for example, when fixed voltage of 1 V is applied between the first and second pumping electrodes 312 and 313 while the pumping cell 310 is heated at 700° C., the oxygen partial pressure in the sealing space 140 drops to approximately $2.15 \times 10^{-10}$ atmospheric pressure. Since this may be a state in which the oxygen is not actually present as atmospheric pressure corresponding to approximately 2 ppb, the hydrogen sensor device 100 according to the present invention, which includes the pumping unit 120 may measure the accurate concentration of the hydrogen gas without interference of the oxygen gas. In order to accurately measure the concentration of the hydrogen gas, it is preferable to operate the pumping unit 120 so that the concentration of the oxygen in the sealing space 140 becomes approximately hundreds or thousands of ppm.

Meanwhile, since the pumping cell 310 of FIG. 11 is a kind of solid electro-chemical oxygen sensor, the pumping unit 120 may be used as a purpose for measuring the concentration of the oxygen gas in the sealing space 140. That is, when the electromotive force between the first and second pumping electrodes 312 and 313 is measured by using an electromotive force measuring unit (not illustrated) which is separately provided instead of applying the voltage or current between the first and second pumping electrodes 312 and 313 of the oxygen ion conductor 311 from the pumping power supply 340, oxygen gas partial pressure $Po_2$ in the sealing space 140 may be calculated by an equation (4) given below.

$$Po_2 = 0.21 \times \exp(4FE/RT) \quad (4)$$

In Equation (4), since R represents the gas constant, F represents the Faraday constant, and T represents the measurement temperature and all of R, T, and F are the constants, the oxygen gas partial pressure in the sealing space 140 may be calculated from the electromotive force E value between the first and second pumping electrodes 312 and 313 measured by using the electromotive force measuring unit. An oxygen gas concentration sensing characteristic of the pumping unit 120 may be used to measure the concentration of the hydrogen gas by using the sensor unit 110 when the oxygen gas partial pressure in the sealing space 140 decreases to a predetermined value or less and such a measurement method will be described below by using FIG. 18.

Further, although not illustrated in FIG. 1, a filling material may be filled in the housing 130 of the hydrogen gas sensor 100 according to the present invention. When the filling material is filled in the housing 130 as such, high heat generated from the heating units 230 and 330 is interrupted from being transferred to other components such as the housing body 131 or the gas separation film 132 and temperatures of the sensor units 110, 510, 610, 710, 810, and 910 and the pumping unit 120 are constantly maintained and in particular, an effective volume in the sealing space 140 decreases, and as a result, a reaction time of the hydrogen sensor device 100 is shortened. As the filling material, ceramic powder or metal power such as alumina, or the like may be used.

MODE FOR INVENTION

A hydrogen sensor device 200 according to a second embodiment of the present invention will be described with reference to FIGS. 12 and 13. The hydrogen sensor device 200 according to the second embodiment of the present invention is different from the hydrogen sensor device according to the first embodiment in that the sensor unit and the pumping unit are integrally formed.

Figure 12:
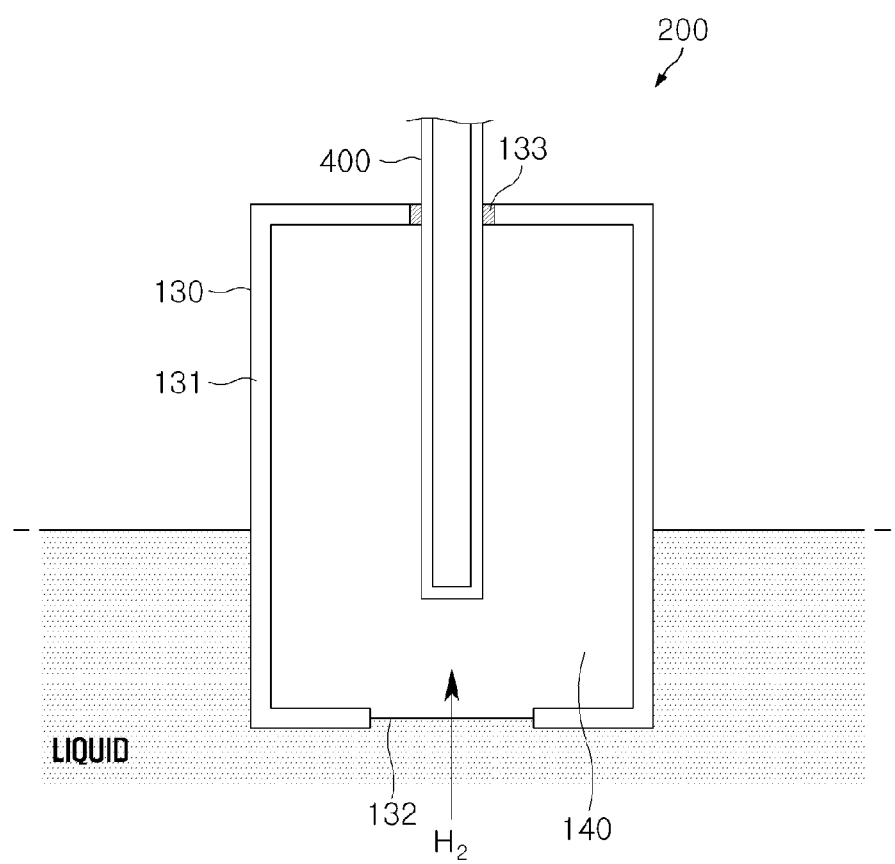
FIG. 12 is a schematic cross-sectional view of a hydrogen sensor device according to a second embodiment of the present invention.

FIG. 12 is a schematic cross-sectional view of a hydrogen sensor device according to a second embodiment of the present invention and referring to FIG. 12, the hydrogen sensor device 200 according to the second embodiment of the present invention is configured to include a sensor unit 400 and the housing 130. Herein, the sensor unit 400 is a component that simultaneously performs a function to discharge the oxygen gas in the sealing space 140 to the outside, that is, a function of the pumping unit 120 of the first embodiment together with a hydrogen sensor function for measuring a concentration of ambient hydrogen gas, that is, the same function as the sensor unit 110 of the first embodiment and may perform an oxygen sensor function for measuring the concentration of the oxygen gas in the sealing space 140 as described above.

Further, the housing 130 is a component for forming the sealing space 140 that isolates one end of the sensor unit 400 from the liquid and the external air and the sensor unit 400 is isolated from the liquid by the housing 130, but the dissolved hydrogen gas penetrates into the sealing space 140 through the gas separation film 132 provided in at least a part inserted into the liquid of the housing 130. As a result, the sensor unit 400 may measure the concentration of the dissolved hydrogen gas without directly contacting the liquid. Since other components except for the sensor unit 400 are similar to those of the hydrogen sensor device 100 according to the first embodiment, a preferable structure of the sensor unit 400 according to the second embodiment will be below described in detail with reference to FIG. 13.

Figure 13:
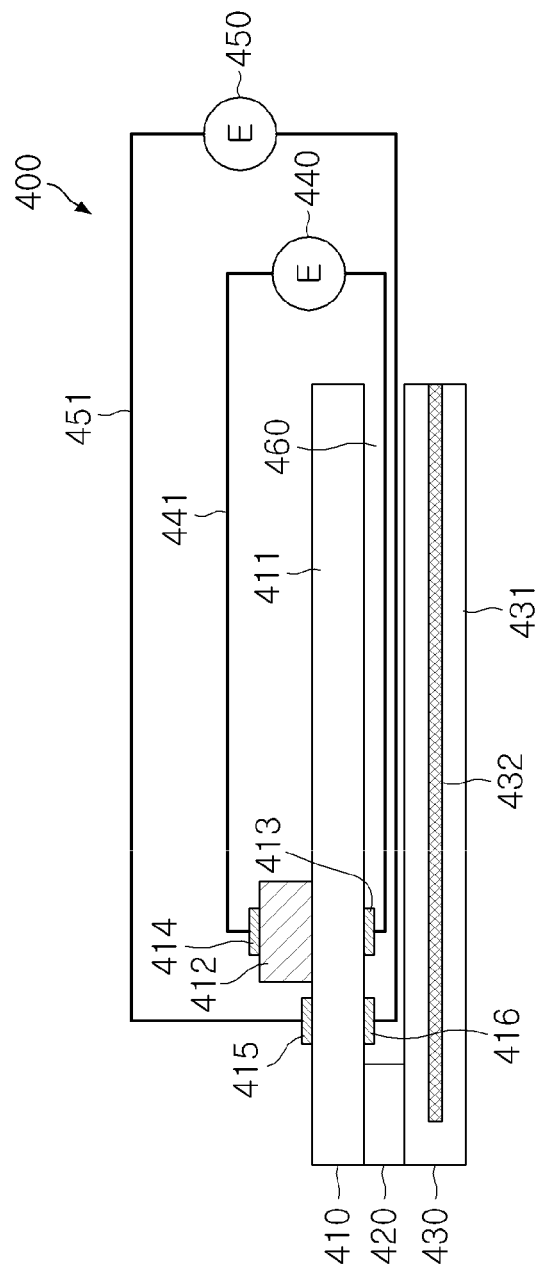
FIG. 13 is a schematic cross-sectional view of a sensor unit according to the second embodiment of the present invention.

As illustrated in FIG. 13, the sensor unit 400 may include a sensing unit 410 including an oxygen ion conductor 411, a hydrogen ion conductor 412 attached to one surface of the oxygen ion conductor 411, a reference electrode 413 formed on the other surface of the oxygen ion conductor 412, that is, at a reference gas passage 460, and a sensing electrode 414 formed on the surface of the hydrogen ion conductor 412, a heater unit 430 for heating the sensing unit 410 apart at a predetermined temperature, and a spacer 420 spacing the sensing unit 410 and the heater unit 430 by a predetermined interval and forming the reference gas passage 460 therebetween. The reference electrode 413 and the sensing electrode 414 are electrically connected to an electromotive force measuring unit 440 through a lead wire 441 to measure the concentration of the hydrogen gas by electromotive force measurement and a principle thereof is similar to the description in the first embodiment.

The spacer 420 as a component inserted between the sensing unit 410 and the heater unit 430 to form the reference gas passage 460 so that the reference electrode 413 is in communication with reference gas may be made of alumina. In this case, the reference gas is preferably external air.

The heater unit 430 as a component for heating the sensing unit 410 up to a sensing temperature may be a form in which a heater wire 432 is formed on a heater substrate 431 made of an insulating substance such as alumina, or the like and such a configuration is similar to of that of the heater unit 230 of the first embodiment.

The sensor unit 400 according to the second embodiment of the present invention is configured to perform a function of the pumping unit that discharges the oxygen gas in the sealing space 140 through the reference gas passage 460 to the outside. A first pumping electrode 415 is formed on one surface (that is, one surface exposed to the sealing space) of a direction in which the hydrogen ion conductor 412 of the oxygen ion conductor 411 is formed and a second pumping electrode 416 is formed on the other surface exposed to the reference gas passage 460 of the oxygen ion conductor 411, and the first and second pumping electrodes 415 and 416 are connected to the pumping power supply 450 by the lead wire 451. In this case, the second pumping electrode 416 is not separately formed and the reference electrode 413 may be used as the second pumping electrode 416.

The sensor unit 400 having such a structure is coupled to the housing 130 while being sealed by the sealing member 133 as illustrated in FIG. 12 and in this case, the hydrogen ion conductor 412 and the sensing electrode 414, and the first pumping electrode 415 are included in the sealing space 140. While the hydrogen sensor device 200 having such a configuration is inserted into the liquid as illustrated in FIG. 12, when voltage or current is applied between the first and second pumping electrodes 415 and 416 by the pumping power supply 450 so that the second pumping electrode 416 becomes positive (+), the oxygen gas that is present in the sealing space 140 is discharged to the outside through the reference gas passage 460. The discharge of the oxygen gas is preferably performed until the concentration of the oxygen in the sealing space 140 becomes approximately hundreds or thousands of ppm.

After a time to discharge the oxygen gas in the sealing space 140 by such a pumping operation and stabilize the hydrogen gas partial pressure in the sealing space 140 elapses, the electromotive force between the reference electrode 413 and the sensing electrode 414 is measured by the electromotive force measuring unit 440 to measure the partial pressure of the hydrogen gas in the sealing space 140 and calculate the concentration of the dissolved hydrogen gas in the liquid from the measured partial pressure.

The hydrogen sensor device 200 according to the second embodiment described as above includes the pumping electrode and the pumping power supply in the sensor unit 400, and as a result, a separate pumping unit needs not be provided. Therefore, the hydrogen sensor device 200 has a simpler structure than the hydrogen sensor device 100 according to the first embodiment. Further, similarly to the description in the first embodiment, the electromotive power between the first pumping electrode 415 and the second pumping electrode 416 is measured to measure the partial pressure of the hydrogen gas in the sealing space 140 by Equation (4) and when a measurement value thereof is larger than a predetermined reference value, the voltage or current is applied between the first and second pumping electrodes 415 and 416 by using the pumping power supply 450 to discharge the oxygen gas in the sealing space 140 to the outside.

Figure 14A:
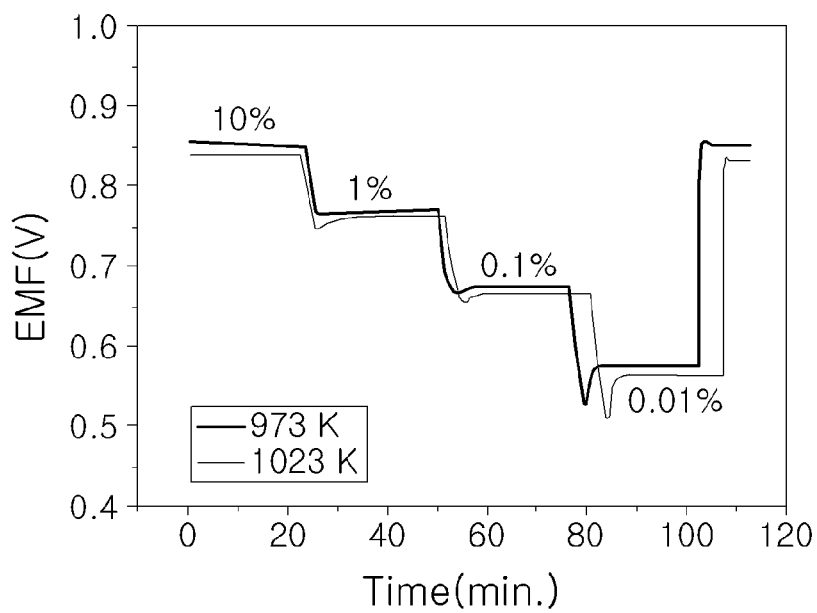
FIGS. 14A and 14B are graphs showing results of measuring a concentration of dissolved hydrogen gas in oil by using the hydrogen sensor device according to the present invention.
Figure 14B:
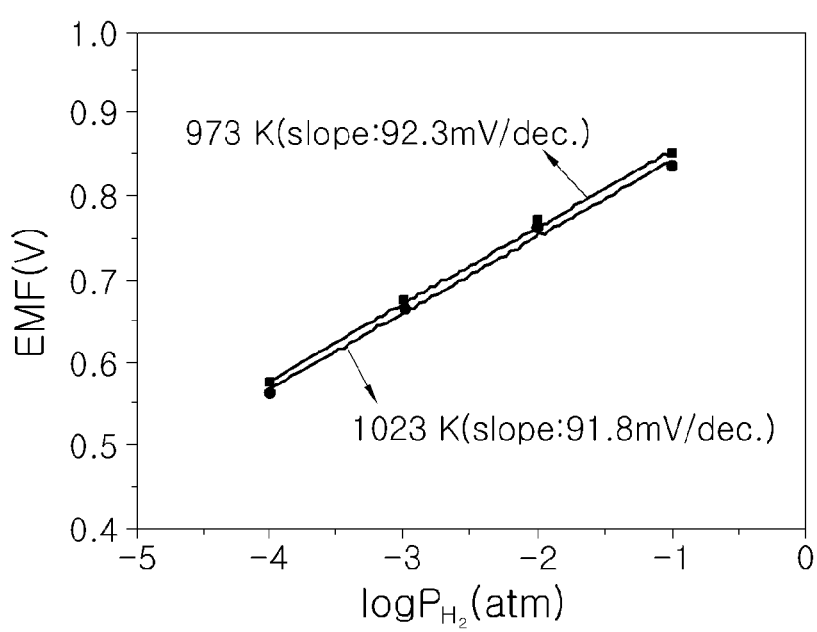

The hydrogen sensor devices 100 and 200 according to the present invention may be used as a wide purpose for measuring the concentration of the dissolved hydrogen gas in the liquid and in particular, usefully used to simply measure whether oil deteriorates in real time by measuring the concentration of the dissolved hydrogen gas in the oil. FIGS. 14A and 14B are graphs showing results of measuring a concentration of dissolved hydrogen gas in oil by using the hydrogen sensor device according to the present invention. FIG. 14A is a graph showing a result of measuring an electromotive force (EMF) value with time while changing the concentration of the hydrogen gas in the oil and FIG. 14B is a graph showing the EMF value as a function of the concentration of the hydrogen gas.

It is verified that from FIGS. 14A and 14B, the EMF value measured by the hydrogen sensor device according to the present invention increases as the concentration of the dissolved hydrogen gas in the oil increases.

Figure 15:
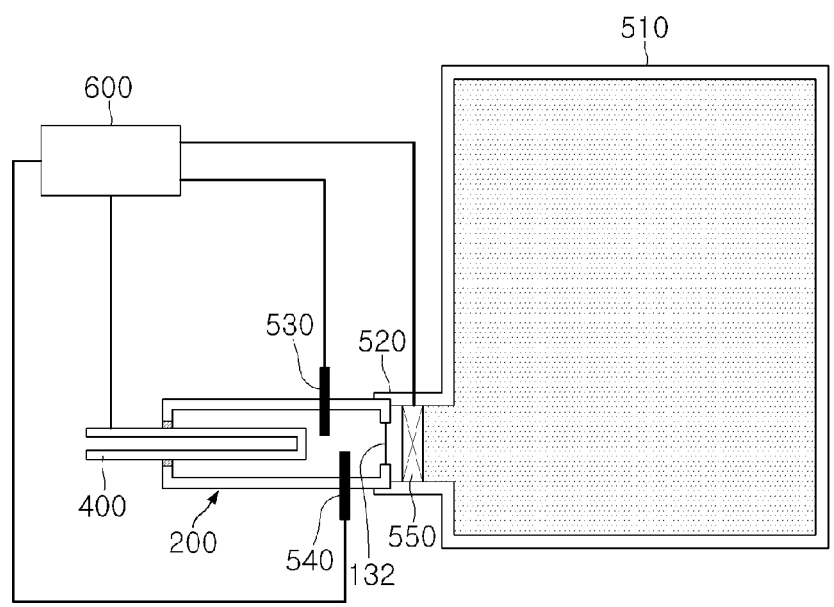
FIG. 15 is a diagram schematically illustrating a state in which the hydrogen sensor device is installed in a container in which liquid to be measured is received according to the second embodiment of the present invention.

The hydrogen sensor devices 100 and 200 according to the present invention may be used by being inserted into the liquid whenever measuring the concentration of the dissolved hydrogen gas in the liquid, but used by being installed in a container containing the liquid. FIG. 15 is a diagram schematically illustrating a state in which the hydrogen sensor device 200 is installed in a container in which liquid to be measured is received according to the second embodiment of the present invention.

Referring to FIG. 15, an opening portion 520 is formed on one side of the container 510 containing the liquid and the hydrogen sensor device 200 according to the present invention is installed in the container 510 so that the gas separation film 132 contacts the opening portion 520. In this case, since the hydrogen sensor device 200 may be attached/detached for a purpose such as repairing or replacing, the hydrogen sensor device 200 is preferably installed to be attached to/detached from the container 510 and in this case, an opening/closing valve 550 capable of opening/closing the opening portion 520 is preferably installed in the opening portion so as to prevent the liquid from flowing out through the opening portion 520. After the hydrogen sensor device 200 is installed in the opening portion, the hydrogen sensor device 200 may be used after opening the opening/closing valve 550 so that the liquid contacts the gas separation film 132 and the opening/closing valve 550 may be manually or automatically opened only during measurement for preventing deterioration of the gas separation film 132.

Figure 16:
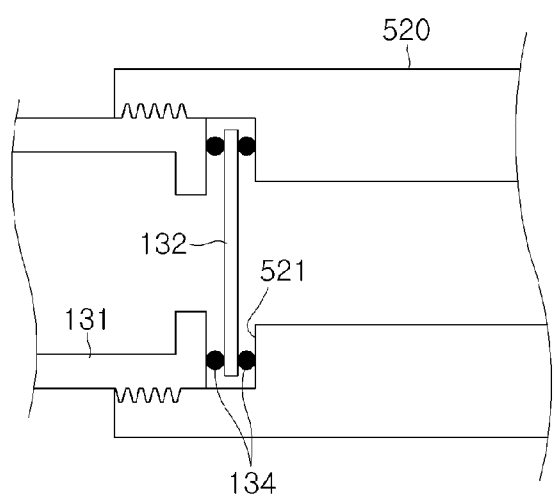
FIG. 16 is a diagram illustrating one example of a method in which the hydrogen sensor device is coupled to the container in which the liquid is received.

As illustrated in FIG. 15, when the hydrogen sensor device 200 is installed in the container 510, since it is not preferable that the external air flows in or the liquid flows out through a coupling portion of the opening portion 520 and the hydrogen sensor device 200, the hydrogen sensor device 200 and the opening portion 520 may be coupled to each other to be gaseously and liquidly sealed and FIG. 16 is a diagram illustrating one example of such a coupling method. As illustrated in FIG. 16, a stepped portion 521 is formed in the opening portion 520 and the sealing material 134 such as the O-ring, or the like may be inserted between the housing body 131 and the gas separation film 132 and between the stepped portion 521 and the gas separation film 132. When FIG. 16 is compared with FIG. 10, in the case of a coupling structure of FIG. 16, the opening portion 520 may serve as the fixing cap 135 of FIG. 10. In this case, the thread is formed in the opening portion 520 and the housing body 131 to be screw-fastened. However, this is just an example and various coupling methods including providing a separate fastening member (not illustrated) outside the housing body 131 and the opening portion 520, and the like may be used.

An installation structure of the hydrogen sensor device 200 illustrated in FIG. 15 is particularly useful when intending to periodically or aperiodically measure the concentration of the dissolved hydrogen gas while installing the hydrogen sensor device 200 in the container containing the liquid. For example, it is preferable to periodically check whether oils of various mechanical devices, for example, transformer oil, and the like deteriorates and when the hydrogen sensor device 200 is installed in the transformer by the method illustrated in FIG. 15, it is possible to conveniently perform the measurement without inserting the hydrogen sensor device 200 into the transformer oil every measurement. In FIG. 15, even though the case in which the hydrogen sensor device 200 according to the second embodiment is installed is described as an example, it is apparent that the hydrogen sensor device 100 according to the first embodiment may also be used by the same method.

In FIG. 15, it is illustrated that the opening portion 520 is formed on the side of the container 510, but the present invention is not limited thereto and the opening portion 520 may be formed on the top or the bottom of the container 510. When the opening portion 520 is formed on the top of the container 510, the gas separation film 132 may not directly contact the liquid, but since the amount of hydrogen which is dissolved in the liquid is in proportion to a root square of partial pressure of evaporated hydrogen according to the Sievert rule, the partial pressure of the hydrogen that enters by penetrating the gas separation film 132 is measured to calculate the concentration of the dissolved hydrogen gas by the same principle. When the opening portion 520 is formed on the top of the container 510, it is advantageous that the opening/closing valve 550 may be omitted.

Meanwhile, when the hydrogen sensor device 200 is installed in the container 510, it is preferable to install a control device 600 for controlling an operation of the hydrogen sensor device 200 overall together as illustrated in FIG. 15. The control device 600 as a component connected to the sensor unit 400 of the hydrogen sensor device 200 to control the overall operation of the sensor unit 400 selectively additionally includes a temperature sensor 530 for measuring a temperature around the sensor unit 400 and a liquid inflow sensor 540 for sensing whether the liquid flows in around the gas separation film 132 in the hydrogen sensor device 200 and the sensors 530 and 540 may be connected to the control device 600. Further, the control device 600 is installed even to the opening/closing valve 550 installed in the opening portion 520 of the container 510 to control an opening/closing operation of the opening/closing valve 550. As the temperature sensor 530, a thermistor, a thermocoupler, a Pt resistance temperature sensor, and the like may be used.

Figure 17:
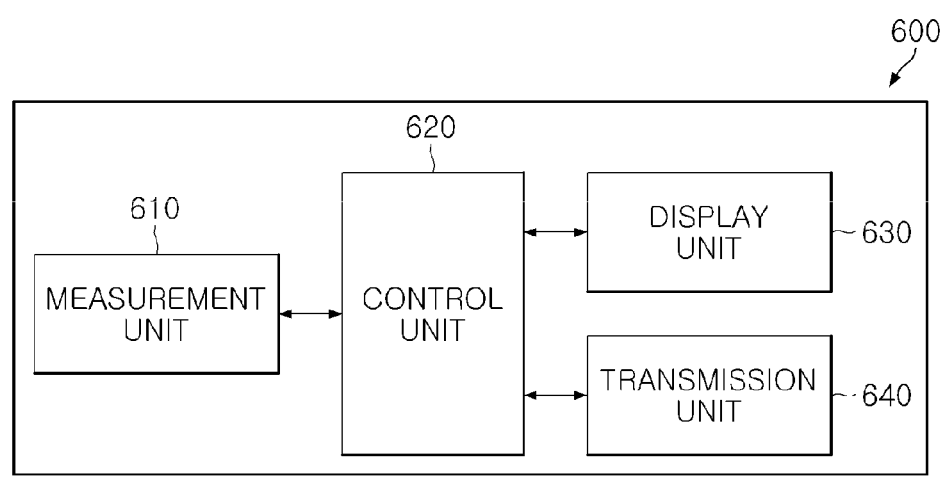
FIG. 17 is an exemplary functional block diagram of a control device.

FIG. 17 is an exemplary functional block diagram of the control device 600 and the control device 600 may include a measurement unit 610, a control unit 620, a display unit 630, and a transmission unit 640. The measurement unit 610 is electrically connected to the sensor unit 400, the temperature sensor 530, the liquid inflow sensor 540, and the like to receive measurement results of the respective sensors and provide the received measurement results to the control unit 620. The control unit 620 as a component for controlling the operation of the hydrogen sensor device 200 based on the measurement result of the measurement unit 610 may, for example, control the heater unit 430 of the hydrogen sensor device 200 so that the sensor unit 400 reaches a predetermined measurement temperature after receiving the temperature measured by the temperature sensor 530, decide or control whether to discharge the oxygen gas in the sealing space 140 or whether to start measuring the concentration of the hydrogen after receiving a measurement result of the oxygen gas partial pressure in the sealing space 140 through measuring the electromotive force between the first and second pumping electrodes 415 and 416, or calculate the concentration of the dissolved hydrogen gas by receiving the measurement result of the partial pressure of the hydrogen gas and thereafter, control the calculated concentration to be displayed in the display unit 630 or to be transmitted by a wired/wireless method through the transmission unit 640. Further, in the case where the liquid inflow sensor 540 is provided, when the control device 600 receives a sensing result of the liquid inflow sensor 540 through the measurement unit 610 and determines that the liquid flows into the sealing space 140, the control device 600 may control the inflow of the liquid to be displayed in the display unit 630 or to be transmitted by the wired/wireless method by using the transmission unit 640. Further, a separate warning unit (not illustrated) is provided except for the display unit 630 to generate a warning sound announcing that the liquid flows in and in this case, the control unit 620 preferably stops the operations of the hydrogen gas sensors 100 and 200.

Figure 18:
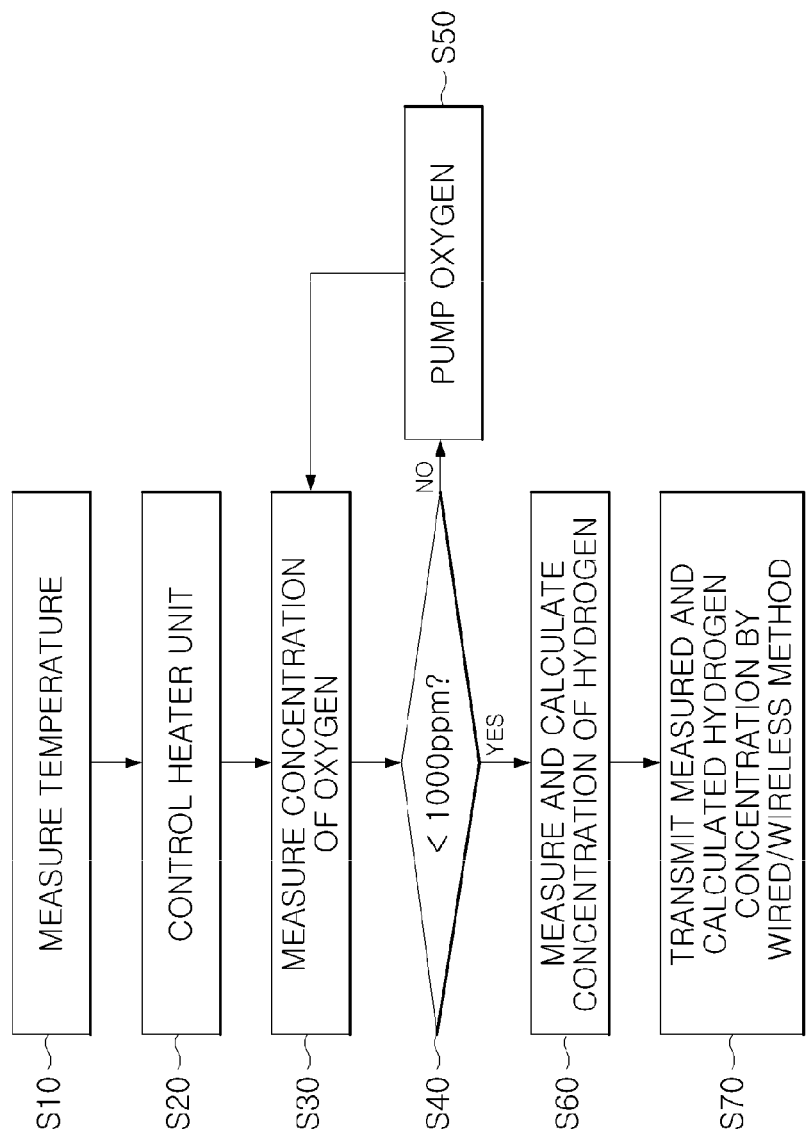
FIG. 18 is an exemplary flowchart of a method for measuring a concentration of hydrogen gas according to the present invention.

FIG. 18 is an exemplary flowchart of a method for measuring a concentration of dissolved hydrogen gas according to the present invention. Referring to FIG. 18, the method for measuring a concentration of dissolved hydrogen gas according to the present invention may include measuring a temperature of a sensor unit 400 by using a temperature sensor 530 (S10), controlling a heater unit 430 so as to reach a predetermined measurement temperature based on a measured temperature value (S20), measuring a concentration of oxygen gas in a sealing space 140 (S30), determining whether the measured concentration of the oxygen gas is equal to or lower than a set value, for example, 1000 ppm (S40), pumping the oxygen gas and discharging the oxygen gas in the sealing space 140 to the outside when the measured concentration is equal to or higher than 1000 ppm according to a result of the determination in step S40 (S50), measuring a concentration of hydrogen gas when the concentration of the oxygen gas is equal to or lower than 1000 ppm according to the result of the determination in step S40 (S60), and transmitting the measured concentration of the hydrogen gas through a transmission unit by a wired or wireless method (S70).

According to the measurement method, since the measurement may start after reaching a predetermined measurement condition, that is, a preferable measurement temperature and the concentration of the oxygen gas in the sealing space, accuracy and reproducibility of the measurement may be secured. Of course, all steps of FIG. 18 do not need to be similarly performed for measuring the concentration of the dissolved hydrogen gas according to the present invention and some steps may be omitted or modified.

The method for measuring the dissolved hydrogen gas according to the present invention may be periodically performed. That is, when the control device 600 is provided with a timer to determine that a measurement period is reached, the steps of FIG. 18 may be programmed to be sequentially performed. In this case, since a measurement result is transmitted to a user in a remote place by the wired or wireless method, for example, it is advantageous that whether oil deteriorates may be more systematically managed.

In the aforementioned embodiments, a housing coupled with the sensor unit while including a gas separation film is described as a required component of the hydrogen sensor device, but the sensor unit may be used to directly contact the liquid without the housing according to the liquid to be measured, a measurement purpose, and the like. That is, a hydrogen sensor device according to a third embodiment of the present invention is characterized in that the housing is omitted from the hydrogen sensor device according to the first and second embodiments. According to the hydrogen sensor device according to the third embodiment of the present invention, since a sensing electrode is inserted into the liquid such as oil, or the like to directly contact the dissolved hydrogen gas in the liquid, it is advantageous that a reaction time is improved without waiting until hydrogen partial pressure in the sealing space in the housing establishes a balance.

In a hydrogen sensor device according to a fourth embodiment of the present invention, similarly to the third embodiment, the housing is omitted in the first and second embodiments and instead, at least a protecting material 710 covering the sensing electrode is provided in order to prevent the sensing electrode from directly contacting the liquid. The hydrogen sensor device 700 according to the fourth embodiment in which the sensing electrode 214 of the sensor unit 110 according to the first embodiment, which is illustrated in FIG. 2 is covered with the protecting material 710 is illustrated in FIG. 19.

Figure 19:
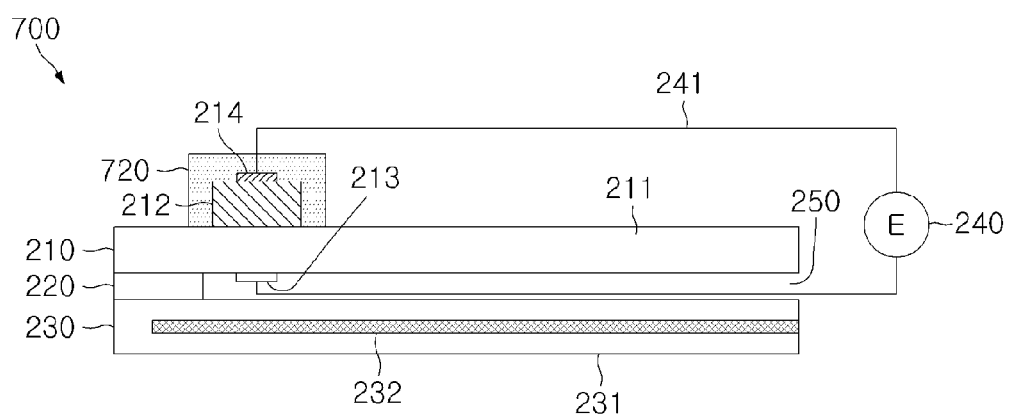
FIG. 19 is a schematic cross-sectional view of a hydrogen sensor device according to a fourth embodiment of the present invention.

When the protecting material 710 is formed to cover the sensing electrode 214 as illustrated in FIG. 19, it is at least advantageous to constantly maintain a temperature of the sensing unit 230 by preventing the sensing unit 210 heated by the heater unit 230 from losing heat to the outside and an additional effect to prevent the deterioration from being promoted through the direct contact of the sensing electrode 214 with the liquid may be expected.

Since the hydrogen gas in the liquid needs to reach the sensing electrode 214 in order for the hydrogen sensor device 700 according to the fourth embodiment of the present invention to measure the concentration of the hydrogen gas in the liquid, the protecting material 710 needs to be at least a component through which the hydrogen gas may pass and to this end, the protecting material 710 may be formed by a porous structure including multiple porosities, for example, a polymer material, a porous ceramic, porous graphite, or metal powder having the porous structure or a glass membrane layer having selective permeability to the hydrogen gas. Since the protecting material 710 is inserted into the liquid, the protecting material 710 needs to be made of a substance which has a sufficient strength to maintain a shape thereof and since the protecting material 710 should not be melted in or reacted with the liquid to be measured, the protecting material 710 needs to be formed by selecting an appropriate substance according to a type of the liquid.

In FIG. 19, it is described that the protecting material 710 is formed in the sensor unit 110 according to the first embodiment of the present invention, but this is just an example and the protecting material 710 may be formed in the sensor unit 400 according to the second embodiment of the present invention, of course. In this case, the protecting material 710 is preferably formed to cover both the sensing electrode 414 and the first pumping electrode 415.

The present invention has been described with reference to the limited embodiments and drawings hereinabove, but it is apparent to those skilled in the art that various modifications can be made within the scope of the technical spirit of the present invention. Accordingly, a protection scope of the present invention should be determined according to disclosures of claims and a scope equivalent thereto.

INDUSTRIAL APPLICABILITY

The hydrogen sensor device according to the present invention can be usefully used to sense whether the oil of various mechanical devices, such as the transformer oil, and the like deteriorates.

The invention claimed is:

1. A hydrogen sensor device for measuring a concentration of dissolved hydrogen gas in liquid, the hydrogen sensor device comprising:
    a sensor unit measuring a concentration of hydrogen gas; and
    a housing coupled to the sensor unit and including a housing body having an opening portion formed in at least a part thereof and a gas separation film coupled to the opening portion to be liquidly sealed,
    wherein a sealing space isolated from the liquid and external air is formed in the housing by the housing body and the gas separation film, and
    the gas separation film penetrates the dissolved hydrogen gas in the liquid into the sealing space,
    wherein the sensor unit includes:
        a hetero-assembly of an oxygen ion conductor and a hydrogen ion conductor,
        a sensing electrode formed on the surface of the hydrogen ion conductor,
        a reference electrode formed on the surface of the oxygen ion conductor, and
        an electromotive force measuring unit measuring electromotive force between the reference electrode and the sensing electrode,
    wherein the sensing electrode is exposed to the sealing space,
    wherein the reference electrode is in communication with the external air or is covered with a reference substance that fixes oxygen partial pressure at the reference electrode side, and
    wherein as the concentration of the dissolved hydrogen gas is changed, the electromotive force is changed.

2. The hydrogen sensor device of claim 1, further comprising:
    a pumping unit pumping oxygen in the sealing space to the outside to remove the oxygen,
    wherein the pumping unit is coupled to the housing.

3. The hydrogen sensor device of claim 2, wherein the pumping unit is integrally formed with the sensor unit.

4. The hydrogen sensor device of claim 1 or 2, further comprising:
    a fixing cap for coupling the gas separation film to the housing.

5. The hydrogen sensor device of claim 1 or 2, wherein the sealing space in the housing is filled with a filling material.

6. The hydrogen sensor device of claim 1 or 2, further comprising:
    a heater for heating the sensor unit up to a sensing temperature.

7. The hydrogen sensor device of claim 1 or 2, wherein the hydrogen sensor device is a hydrogen sensor device coupled to an opening portion of a container containing the liquid to measure the concentration of the dissolved hydrogen gas in the liquid contained in the container, and wherein the gas separation film is in communication with the inside of the container through the opening portion to penetrate the dissolved hydrogen gas in the liquid into the sealing space.

8. The hydrogen sensor device of claim 7, wherein while a sealing member is inserted between the gas separation film and the opening portion and between the housing body and the gas separation film, the sealing member is coupled to the opening portion.

9. The hydrogen sensor device of claim 7, further comprising:

at least one of a temperature sensor for measuring a temperature of the sensor unit and a liquid inflow sensor for sensing whether the liquid flows in.

10. A hydrogen sensor device for measuring a concentration of dissolved hydrogen gas in liquid, the hydrogen sensor device comprising:

a sensor unit measuring a concentration of hydrogen gas;
a housing coupled to the sensor unit and including a housing body having an opening portion formed in at least a part thereof and a gas separation film coupled to the opening portion to be liquidly sealed, a sealing space isolated from the liquid and external air being formed in the housing by the housing body and the gas separation film, the gas separation film penetrating the dissolved hydrogen gas in the liquid into the sealing space; and
a pumping unit pumping oxygen in the sealing space to the outside to remove the oxygen, the pumping unit being coupled to the housing,
wherein the pumping unit includes:
an oxygen ion conductor,
a heater substrate spaced apart from the oxygen ion conductor with a predetermined interval by a spacer, the spaced interval being provided to be in communication with the external air,
a first pumping electrode formed on one surface of the oxygen ion conductor at the sealing space side,
a second pumping electrode formed on one surface of the oxygen ion conductor at the external air side, and
a pumping power supply applying voltage or current between the first pumping electrode and the second pumping electrode, and
wherein the voltage or current is applied between the first pumping electrode and the second pumping electrode by the pumping power supply to pump oxygen at the sealing space side to the external air side.

11. A hydrogen sensor device for measuring a concentration of dissolved hydrogen gas in liquid, the hydrogen sensor device comprising:

a sensor unit measuring a concentration of hydrogen gas;
a housing coupled to the sensor unit and including a housing body having an opening portion formed in at least a part thereof and a gas separation film coupled to the opening portion to be liquidly sealed, a sealing space isolated from the liquid and external air being formed in the housing by the housing body and the gas separation film, the gas separation film penetrating the dissolved hydrogen gas in the liquid into the sealing space; and
a pumping unit pumping oxygen in the sealing space to the outside to remove the oxygen, the pumping unit being coupled to the housing,
wherein the pumping unit is integrally formed with the sensor unit,
wherein the sensor unit includes:
an oxygen ion conductor,
a heater substrate spaced apart from the oxygen ion conductor with a predetermined interval by the spacer, the spaced interval being provided to be in communication with the external air,
a hydrogen ion conductor attached to at least a part of the oxygen ion conductor exposed to the sealing space side,
a sensing electrode formed on the surface exposed to the sealing space of the hydrogen ion conductor,
a reference electrode formed on the surface of the oxygen ion conductor at the external air side,
an electromotive force measuring unit measuring the electromotive force between the reference electrode and the sensing electrode,
a first pumping electrode formed on the surface of the sealing space side which is not attached to the hydrogen ion conductor of the oxygen ion conductor,
a second pumping electrode formed on the surface of the oxygen ion conductor at the external air side, and
a pumping power supply applying the voltage between the first pumping electrode and the second pumping electrode,
wherein as the concentration of the dissolved hydrogen gas is changed, the electromotive force is changed, and
wherein the voltage is applied between the first pumping electrode and the second pumping electrode by the pumping power supply to pump the oxygen at the sealing space side to the external air side.

12. The hydrogen sensor device of claim 11, wherein the reference electrode and the second pumping electrode are one electrode.

13. A dissolved hydrogen measuring device for measuring a concentration of dissolved hydrogen gas in liquid contained in a container, the dissolved hydrogen measuring device comprising:

a hydrogen sensor device coupled to an opening portion provided at one side of the container, the hydrogen sensor device including:
a sensor unit measuring a concentration of hydrogen gas,
a housing coupled to the sensor unit, the housing including a housing body having an opening portion formed in at least a part thereof and a gas separation film coupled to the opening portion to be liquidly sealed and having a sealing space isolated from the liquid and external air therein, and
a pumping unit pumping oxygen in the sealing space to the outside to remove the oxygen, the pumping unit being configured to include an oxygen ion conductor, a first pumping electrode on one surface of the oxygen ion conductor at the sealing space side and a second pumping electrode on the external surface of the oxygen ion conductor at the external air side; and
a control device electrically connected to the sensor unit to control an operation of the sensor unit,
wherein the gas separation film is in communication with the inside of the container through the opening portion to penetrate the dissolved hydrogen gas in the liquid into the sealing space, wherein the control device includes:
- a measurement unit receiving a measurement result from the sensor unit,
- a control unit controlling an operation of the hydrogen sensor device,
- a display unit displaying the measured concentration of the dissolved hydrogen gas, and
- a transmission unit transmitting a result of the measurement of the concentration of the dissolved hydrogen gas by a wired or wireless method, and wherein the control unit controls an operation of the pumping unit.

14. The dissolved hydrogen measuring device of claim 13, wherein the hydrogen sensor device is coupled to the opening portion to be attached/detached.

15. The dissolved hydrogen measuring device of claim 13, further comprising:
a temperature sensor for measuring a temperature of the sensor unit,
wherein the control device receives a temperature sensing result from the temperature sensor.

16. The dissolved hydrogen measuring device of claim 13, wherein an opening/closing valve is installed in the opening portion, and
wherein the control device controls an operation of the opening/closing valve.

17. The dissolved hydrogen measuring device of claim 13, wherein the pumping unit measures electromotive force between the first pumping electrode and the second pumping electrode to perform even an oxygen sensor function to measure partial pressure of oxygen gas in the sealing space, and
wherein the control unit receives a result of measuring the partial pressure of the oxygen gas in the sealing space from the pumping unit that performs the oxygen sensor function and thereafter, controls a pumping operation of the pumping unit based on the result.

18. A method for measuring a concentration of dissolved hydrogen gas in liquid by using a dissolved hydrogen measuring device for measuring a concentration of dissolved hydrogen gas in liquid contained in a container, the method comprising:
measuring the temperature of the sensor unit by using a temperature sensor;
controlling the temperature of the sensor unit to become the measurement temperature based on a result of the measurement temperature; and
measuring partial pressure of hydrogen gas in the sealing space by using the sensor unit and calculating the concentration of the dissolved hydrogen gas by using a result of the measurement,
wherein the dissolved hydrogen measuring device comprises:
a hydrogen sensor device coupled to an opening portion provided at one side of the container, the hydrogen sensor device including:
- a sensor unit measuring a concentration of hydrogen gas; and
- a housing coupled to the sensor unit, the housing including a housing body having an opening portion formed in at least a part thereof and a gas separation film coupled to the opening portion to be liquidly sealed and having a sealing space isolated from the liquid and external air therein, and
a temperature sensor for measuring a temperature of the sensor unit, wherein the control device receives a temperature sensing result from the temperature sensor,
wherein the gas separation film is in communication with the inside of the container through the opening portion to penetrate the dissolved hydrogen gas in the liquid into the sealing space,
wherein the hydrogen sensor device further includes a pumping unit pumping oxygen in the sealing space to the outside to remove the oxygen,
wherein the pumping unit is configured to include an oxygen ion conductor, a first pumping electrode formed on one surface of the oxygen ion conductor at the sealing space side and a second pumping electrode formed on the external surface of the oxygen ion conductor at the external air side,
wherein the pumping unit measures electromotive force between the first pumping electrode and the second pumping electrode to perform even an oxygen sensor function to measure partial pressure of oxygen gas in the sealing space, and
wherein the pumping unit performing the oxygen sensor function performs measuring partial pressure of oxygen gas in the sealing space to determining whether the measured partial pressure of the oxygen gas is equal to or higher than a reference value, controlling the pumping operation of the pumping unit so as to discharge the oxygen gas in the sealing space to the outside when the measured partial pressure of the oxygen gas is equal to or higher than the reference value, and measuring the partial pressure of the hydrogen gas when the measured partial pressure of the oxygen gas is equal to or lower than the reference value.

19. The method of claim 18, further comprising:
transmitting the measured and calculated concentration of the dissolved hydrogen gas by a wired or wireless method.

20. A hydrogen sensor device at least partially inserted into liquid to measure a concentration of dissolved hydrogen gas in the liquid, the hydrogen sensor device comprising:
a sensing unit including a reference electrode and a sensing electrode at both sides of a solid electrolyte;
a reference gas passage for supplying reference gas to the reference electrode while being isolated from the liquid;
a heater unit for heating the sensor unit up to a sensing temperature; and
an electromotive force measuring unit measuring electromotive force between the reference electrode and the sensing electrode,
wherein the sensing electrode is exposed to the dissolved hydrogen gas in the liquid and as the concentration of the dissolved hydrogen gas is changed, the electromotive force is changed,
wherein the solid electrolyte is formed by hetero-junction of an oxygen ion conductor and a hydrogen ion conductor or the hydrogen ion conductor, and
wherein the sensing electrode is formed on the surface of the hydrogen ion conductor.

21. The hydrogen sensor device of claim 20, further comprising:
a protecting material formed to at least cover the sensing electrode,
wherein the protecting material is formed by a porous material or glass ceramic through which hydrogen gas is capable of passing.

22. A hydrogen sensor device at least partially inserted into liquid to measure a concentration of dissolved hydrogen gas in the liquid, the hydrogen sensor device comprising:
- a sensing unit including a reference electrode and a sensing electrode at both sides of a solid electrolyte;
- a reference gas partial pressure fixing reference substance covering the reference electrode to fix reference gas partial pressure at the reference electrode side;
- a heater unit for heating the sensor unit up to a sensing temperature; and
- an electromotive force measuring unit measuring electromotive force between the reference electrode and the sensing electrode,
- wherein the sensing electrode is exposed to the dissolved hydrogen gas in the liquid and as the concentration of the dissolved hydrogen gas is changed, the electromotive force is changed,
- wherein the solid electrolyte is formed by hetero-junction of an oxygen ion conductor and a hydrogen ion conductor or the hydrogen ion conductor, and
- wherein the sensing electrode is formed on the surface of the hydrogen ion conductor.

23. The hydrogen sensor device of claim 22, further comprising: a protecting material formed to at least cover the sensing electrode, wherein the protecting material is formed by a porous material or glass ceramic through which hydrogen gas is capable of passing.

* * * * *